(12) United States Patent
Goode et al.

(10) Patent No.: US 11,819,683 B2
(45) Date of Patent: Nov. 21, 2023

(54) MODULAR STIMULATION SYSTEM FOR THE TREATMENT OF GASTROINTESTINAL DISORDERS

(71) Applicant: EndoStim, Inc., Dallas, TX (US)

(72) Inventors: Paul V. Goode, Round Rock, TX (US); Virender K. Sharma, Paradise Valley, AZ (US); Shai Policker, Tenafly, NJ (US)

(*) Notice: Subject to any disclaimer, the term of this patent is extended or adjusted under 35 U.S.C. 154(b) by 0 days.

(21) Appl. No.: 15/816,631

(22) Filed: Nov. 17, 2017

(65) Prior Publication Data

US 2018/0154135 A1 Jun. 7, 2018

Related U.S. Application Data

(60) Provisional application No. 62/423,334, filed on Nov. 17, 2016.

(51) Int. Cl.
*A61N 1/05* (2006.01)
*A61N 1/36* (2006.01)
*A61N 1/375* (2006.01)

(52) U.S. Cl.
CPC ......... *A61N 1/0507* (2013.01); *A61N 1/0509* (2013.01); *A61N 1/3606* (2013.01);
(Continued)

(58) Field of Classification Search
CPC .. A61N 1/0507; A61N 1/0509; A61N 1/3606; A61N 1/36034; A61N 1/36007;
(Continued)

(56) References Cited

U.S. PATENT DOCUMENTS 3,909,883 A 10/1975 Fegen
3,910,281 A 10/1975 Kletschka
(Continued)

FOREIGN PATENT DOCUMENTS

CN 1476339 2/2004
CN 1494451 A 5/2004
(Continued)

OTHER PUBLICATIONS

International Search Report for PCT/US2017/062298, dated Feb. 1, 2018.
(Continued)

*Primary Examiner* — Nathan J Jenness
(74) *Attorney, Agent, or Firm* — Novel IP

(57) ABSTRACT

Systems and methods for treating a gastrointestinal condition of a patient includes minimally invasively implanting a modular stimulator system in a patient's treatment site. The modular stimulator system comprises a microstimulator module, a small power source module and a macrostimulator module that are detachably attachable to each other. For the first phase of treatment, the microstimulator module and power source are implanted with a stimulating electrode proximate a target tissue. Electrical stimulation is provided for a short period of time and treatment efficacy is evaluated through clinical results and patient reporting. If therapy is not effective, stimulation parameters can be changed and/or the implantation site can be moved. If therapy is effective, portions of the microstimulator module and/or small power source are replaced with the macrostimulator module for long term therapy of the second phase of treatment.

17 Claims, 8 Drawing Sheets

(52) U.S. Cl.
CPC ..... *A61N 1/36007* (2013.01); *A61N 1/36031* (2017.08); *A61N 1/36034* (2017.08); *A61N 1/36053* (2013.01); *A61N 1/3752* (2013.01)

(58) Field of Classification Search
CPC ............ A61N 1/36053; A61N 1/36031; A61N 1/3752
USPC .............................................. 607/40, 41, 133
See application file for complete search history.

(56) References Cited

U.S. PATENT DOCUMENTS

| | | | |
|---|---|---|---|
| 4,393,883 | A | 7/1983 | Smyth |
| 4,414,986 | A | 11/1983 | Dickhudt |
| 4,612,934 | A | 9/1986 | Borkan |
| 4,735,205 | A | 4/1988 | Chachques |
| 5,117,827 | A | 6/1992 | Stuebe |
| 5,188,104 | A | 2/1993 | Wernicke |
| 5,193,539 | A | 3/1993 | Schulman |
| 5,197,491 | A | 3/1993 | Anderson |
| 5,231,988 | A | 8/1993 | Wernicke |
| 5,263,480 | A | 11/1993 | Wernicke |
| 5,292,344 | A | 3/1994 | Douglas |
| 5,360,428 | A | 11/1994 | Hutchinson, Jr. |
| 5,423,872 | A | 6/1995 | Cigaina |
| 5,531,778 | A | 7/1996 | Maschino |
| 5,540,730 | A | 7/1996 | Terry, Jr. |
| 5,556,425 | A | 9/1996 | Hewson |
| 5,606,242 | A | 2/1997 | Hull |
| 5,633,573 | A | 5/1997 | van Phuoc |
| 5,649,902 | A | 7/1997 | Yoon |
| 5,674,205 | A | 10/1997 | Pasricha |
| 5,690,691 | A | 11/1997 | Chen |
| 5,697,375 | A | 12/1997 | Hickey |
| 5,709,224 | A | 1/1998 | Behl |
| 5,716,385 | A | 2/1998 | Mittal |
| 5,716,392 | A | 2/1998 | Bourgeois |
| 5,769,881 | A | 6/1998 | Schroeppel |
| 5,810,810 | A | 9/1998 | Tay |
| 5,836,994 | A | 11/1998 | Bourgeois |
| 5,861,014 | A | 1/1999 | Familoni |
| 5,861,044 | A | 1/1999 | Crenshaw |
| 5,882,340 | A | 3/1999 | Yoon |
| 5,893,883 | A | 4/1999 | Torgerson |
| 5,935,126 | A | 8/1999 | Riza |
| 5,995,872 | A | 11/1999 | Bourgeois |
| 6,006,755 | A | 12/1999 | Edwards |
| 6,026,326 | A | 2/2000 | Bardy |
| 6,041,258 | A | 3/2000 | Cigaina |
| 6,051,017 | A | 4/2000 | Loeb |
| 6,091,992 | A | 7/2000 | Bourgeois |
| 6,097,984 | A | 8/2000 | Douglas |
| 6,216,039 | B1 | 4/2001 | Bourgeois |
| 6,221,039 | B1 | 4/2001 | Durgin |
| 6,243,607 | B1 | 6/2001 | Mintchev |
| 6,254,598 | B1 | 7/2001 | Edwards |
| 6,285,897 | B1 | 9/2001 | Kilcoyne |
| 6,321,124 | B1 | 11/2001 | Cigaina |
| 6,360,130 | B1 | 3/2002 | Duysens |
| 6,381,495 | B1 | 4/2002 | Jenkins |
| 6,449,511 | B1 | 9/2002 | Mintchev |
| 6,510,332 | B1 | 1/2003 | Greenstein |
| 6,542,776 | B1 | 4/2003 | Gordon |
| 6,571,127 | B1 | 5/2003 | Ben-Haim |
| 6,587,719 | B1 | 7/2003 | Barrett |
| 6,591,137 | B1 | 7/2003 | Fischell |
| 6,606,523 | B1 | 8/2003 | Jenkins |
| 6,611,715 | B1 | 8/2003 | Boveja |
| 6,612,983 | B1 | 9/2003 | Marchal |
| 6,615,084 | B1 | 9/2003 | Cigaina |
| 6,678,561 | B2 | 1/2004 | Forsell |
| 6,684,104 | B2 | 1/2004 | Gordon |
| 6,735,477 | B2 | 5/2004 | Levine |
| 6,749,607 | B2 | 6/2004 | Edwards |
| 6,754,536 | B2 | 6/2004 | Swoyer |
| 6,760,626 | B1 | 7/2004 | Boveja |
| 6,820,019 | B1 | 11/2004 | Kelly |
| 6,826,428 | B1 | 11/2004 | Chen |
| 6,832,114 | B1 | 12/2004 | Whitehurst |
| 6,853,862 | B1 | 2/2005 | Marchal |
| 6,876,885 | B2 | 4/2005 | Swoyer |
| 6,879,859 | B1 | 4/2005 | Boveja |
| 6,879,861 | B2 | 4/2005 | Benz |
| 6,901,295 | B2 | 5/2005 | Sharma |
| 6,915,165 | B2 | 7/2005 | Forsell |
| 6,947,792 | B2 | 9/2005 | Ben-Haim |
| 6,952,613 | B2 | 10/2005 | Swoyer |
| 7,006,871 | B1 | 2/2006 | Darvish |
| 7,016,735 | B2 | 3/2006 | Imran |
| 7,054,689 | B1 | 5/2006 | Whitehurst |
| 7,054,690 | B2 | 5/2006 | Imran |
| 7,076,305 | B2 | 7/2006 | Imran |
| 7,076,306 | B2 | 7/2006 | Marchal |
| 7,087,053 | B2 | 8/2006 | Vanney |
| 7,114,502 | B2 | 10/2006 | Schulman |
| 7,120,498 | B2 | 10/2006 | Imran |
| 7,127,295 | B2 | 10/2006 | Evans |
| 7,146,216 | B2 | 12/2006 | Bumm |
| 7,167,750 | B2 | 1/2007 | Knudson |
| 7,177,693 | B2 | 2/2007 | Starkebaum |
| 7,200,443 | B2 | 4/2007 | Faul |
| 7,203,551 | B2 | 4/2007 | Houben |
| 7,255,675 | B2 | 8/2007 | Gertner |
| 7,263,405 | B2 | 8/2007 | Boveja |
| 7,299,091 | B2 | 11/2007 | Barrett |
| 7,310,557 | B2 | 12/2007 | Maschino |
| 7,340,306 | B2 | 3/2008 | Barrett |
| 7,343,201 | B2 | 3/2008 | Mintchev |
| 7,363,084 | B2 | 4/2008 | Kurokawa |
| 7,444,183 | B2 | 10/2008 | Knudson |
| 7,477,994 | B2 | 1/2009 | Sunshine |
| 7,499,752 | B2 * | 3/2009 | Maschino .......... A61N 1/36082 607/40 |
| 7,519,431 | B2 | 4/2009 | Goetz |
| 7,519,433 | B2 | 4/2009 | Foley |
| 7,558,629 | B2 | 7/2009 | Keimel |
| 7,593,777 | B2 | 9/2009 | Gerber |
| 7,599,736 | B2 | 10/2009 | Dilorenzo |
| 7,620,454 | B2 | 11/2009 | Dinsmoor |
| 7,664,551 | B2 | 2/2010 | Cigaina |
| 7,676,270 | B2 | 3/2010 | Imran |
| 7,702,394 | B2 | 4/2010 | Imran |
| 7,702,395 | B2 | 4/2010 | Towe |
| 7,702,934 | B2 | 4/2010 | Lmran |
| 7,711,437 | B1 | 5/2010 | Bornzin |
| 7,720,539 | B2 | 5/2010 | Mintchev |
| 7,729,771 | B2 | 6/2010 | Knudson |
| 7,734,355 | B2 | 6/2010 | Cohen |
| 7,738,961 | B2 | 6/2010 | Sharma |
| 7,742,818 | B2 | 6/2010 | Dinsmoor |
| 7,794,425 | B2 | 9/2010 | Gobel |
| 7,809,442 | B2 | 10/2010 | Bolea |
| 7,813,809 | B2 | 10/2010 | Strother |
| 7,835,796 | B2 | 11/2010 | Maschino |
| 7,848,802 | B2 | 12/2010 | Goetz |
| 7,890,185 | B2 | 2/2011 | Cohen |
| 7,899,540 | B2 | 3/2011 | Maschino |
| 7,914,468 | B2 | 3/2011 | Shalon |
| 7,941,221 | B2 | 5/2011 | Foley |
| 7,957,807 | B2 | 6/2011 | Starkebaum |
| 7,962,214 | B2 | 6/2011 | Byerman |
| 7,983,755 | B2 | 7/2011 | Starkebaum |
| 8,135,470 | B2 | 3/2012 | Keimel |
| 8,155,758 | B2 | 4/2012 | Roline |
| 8,160,709 | B2 | 4/2012 | Soffer |
| 8,185,206 | B2 | 5/2012 | Starkebaum |
| 8,282,561 | B2 | 10/2012 | Towe |
| 8,380,321 | B2 | 2/2013 | Goetz |
| 8,406,868 | B2 | 3/2013 | Buschman |
| 8,423,134 | B2 | 4/2013 | Buschman |
| 8,447,403 | B2 | 5/2013 | Sharma |
| 8,447,404 | B2 | 5/2013 | Sharma |
| 8,452,407 | B2 | 5/2013 | Whitehurst |
| 8,467,874 | B2 | 6/2013 | Chen |

(56) References Cited

U.S. PATENT DOCUMENTS

| | | |
|---|---|---|
| 8,467,884 B2 | 6/2013 | Chen |
| 8,521,292 B2 | 8/2013 | Wei |
| 8,538,532 B2 | 9/2013 | Starkebaum |
| 8,538,534 B2 | 9/2013 | Soffer |
| 8,543,210 B2 | 9/2013 | Sharma |
| 8,556,952 B2 | 10/2013 | Shadduck |
| 8,594,811 B2 | 11/2013 | Chen |
| 8,712,529 B2 | 4/2014 | Sharma |
| 8,712,530 B2 | 4/2014 | Sharma |
| 8,718,771 B2 | 5/2014 | Gandhi |
| 8,761,903 B2 | 6/2014 | Chen |
| 8,792,986 B2 | 7/2014 | Cigaina |
| 8,831,737 B2 | 9/2014 | Wesselink |
| 8,892,217 B2 | 11/2014 | Camps |
| 9,020,597 B2 | 4/2015 | Sharma |
| 9,037,245 B2 | 5/2015 | Sharma |
| 9,061,147 B2 | 6/2015 | Sharma |
| 9,345,879 B2 | 5/2016 | Sharma |
| 9,498,619 B2 | 11/2016 | Goode |
| 9,724,510 B2 | 8/2017 | Sharma |
| 2001/0041831 A1 | 11/2001 | Starkweather |
| 2002/0103522 A1 | 8/2002 | Swoyer |
| 2002/0138075 A1 | 9/2002 | Edwards |
| 2002/0161414 A1 | 10/2002 | Flesler |
| 2002/0165589 A1 | 11/2002 | Imran |
| 2003/0009202 A1 | 1/2003 | Levine |
| 2003/0014086 A1 | 1/2003 | Sharma |
| 2003/0028226 A1 | 2/2003 | Thompson |
| 2003/0055463 A1 | 3/2003 | Gordon |
| 2003/0078633 A1 | 4/2003 | Firlik |
| 2003/0120321 A1 | 6/2003 | Bumm |
| 2003/0144708 A1 | 7/2003 | Starkebaum |
| 2003/0195600 A1 | 10/2003 | Tronnes |
| 2004/0010290 A1 | 1/2004 | Schroeppel |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 | 3/2004 | Flesler |
| 2004/0059393 A1 | 3/2004 | Policker |
| 2004/0073453 A1 | 4/2004 | Nenov |
| 2004/0088033 A1 | 5/2004 | Smits |
| 2004/0116977 A1 | 6/2004 | Finch |
| 2004/0138586 A1 | 7/2004 | Ganz |
| 2004/0147976 A1 | 7/2004 | Gordon |
| 2004/0167583 A1 | 8/2004 | Knudson |
| 2004/0172088 A1 | 9/2004 | Knudson |
| 2004/0186544 A1 | 9/2004 | King |
| 2004/0193229 A1* | 9/2004 | Starkebaum ............ A61N 1/05 607/40 |
| 2004/0215287 A1* | 10/2004 | Swoyer ............ A61N 1/36071 607/48 |
| 2004/0236381 A1 | 11/2004 | Dinsmoor |
| 2004/0236382 A1 | 11/2004 | Dinsmoor |
| 2004/0243182 A1 | 12/2004 | Cohen |
| 2004/0254622 A1 | 12/2004 | Shadduck |
| 2005/0027328 A1 | 2/2005 | Greenstein |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131485 A1 | 6/2005 | Knudson |
| 2005/0131486 A1 | 6/2005 | Boveja |
| 2005/0137480 A1 | 6/2005 | Alt |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0222638 A1 | 10/2005 | Foley |
| 2005/0245788 A1 | 11/2005 | Gerber |
| 2005/0251219 A1 | 11/2005 | Evans |
| 2006/0004304 A1 | 1/2006 | Parks |
| 2006/0015162 A1 | 1/2006 | Edward |
| 2006/0036293 A1 | 2/2006 | Whitehurst |
| 2006/0041277 A1 | 2/2006 | Deem |
| 2006/0047323 A1 | 3/2006 | Foley |
| 2006/0064037 A1 | 3/2006 | Shalon |
| 2006/0074459 A1 | 4/2006 | Flesler |
| 2006/0089699 A1 | 4/2006 | Imran |
| 2006/0095077 A1 | 5/2006 | Tronnes |
| 2006/0106442 A1 | 5/2006 | Richardson |
| 2006/0116736 A1 | 6/2006 | Dilorenzo |
| 2006/0122660 A1 | 6/2006 | Boveja |
| 2006/0149337 A1 | 7/2006 | John |
| 2006/0167498 A1 | 7/2006 | Dilorenzo |
| 2006/0200217 A1 | 9/2006 | Wessman |
| 2006/0206160 A1 | 9/2006 | Cigaina |
| 2006/0218011 A1 | 9/2006 | Walker |
| 2006/0247717 A1 | 11/2006 | Starkebaum |
| 2006/0247718 A1 | 11/2006 | Starkebaum |
| 2006/0247719 A1 | 11/2006 | Maschino |
| 2006/0247721 A1 | 11/2006 | Maschino |
| 2006/0247722 A1 | 11/2006 | Maschino |
| 2006/0265021 A1 | 11/2006 | Herbert |
| 2006/0270989 A1 | 11/2006 | McMichael |
| 2007/0016274 A1 | 1/2007 | Boveja |
| 2007/0049793 A1 | 3/2007 | Ignagni |
| 2007/0060955 A1 | 3/2007 | Strother |
| 2007/0060968 A1 | 3/2007 | Strother |
| 2007/0060979 A1 | 3/2007 | Strother |
| 2007/0066995 A1 | 3/2007 | Strother |
| 2007/0067000 A1 | 3/2007 | Strother |
| 2007/0100388 A1 | 5/2007 | Gerber |
| 2007/0106337 A1 | 5/2007 | Errico |
| 2007/0106338 A1 | 5/2007 | Errico |
| 2007/0114971 A1 | 5/2007 | Uesaka |
| 2007/0142699 A1 | 6/2007 | Jandrall |
| 2007/0142831 A1 | 6/2007 | Shadduck |
| 2007/0142884 A1 | 6/2007 | Jandrall |
| 2007/0156182 A1 | 7/2007 | Castel |
| 2007/0162084 A1 | 7/2007 | Chen |
| 2007/0162085 A1 | 7/2007 | Dilorenzo |
| 2007/0179542 A1 | 8/2007 | Prakash |
| 2007/0185374 A1 | 8/2007 | Kick |
| 2007/0238942 A1 | 10/2007 | Baylor |
| 2007/0239248 A1 | 10/2007 | Hastings |
| 2007/0244375 A1 | 10/2007 | Jenkins |
| 2007/0255118 A1 | 11/2007 | Miesel |
| 2007/0255335 A1 | 11/2007 | Herbert |
| 2007/0255336 A1 | 11/2007 | Herbert |
| 2007/0255352 A1 | 11/2007 | Roline |
| 2007/0265662 A1 | 11/2007 | Ufford |
| 2007/0265666 A1 | 11/2007 | Roberts |
| 2007/0265668 A1 | 11/2007 | Reinke |
| 2007/0265671 A1 | 11/2007 | Roberts |
| 2007/0265674 A1 | 11/2007 | Olson |
| 2007/0282410 A1 | 12/2007 | Cross |
| 2007/0293910 A1 | 12/2007 | Strother |
| 2007/0299481 A1 | 12/2007 | Syed |
| 2008/0021512 A1 | 1/2008 | Knudson |
| 2008/0039904 A1 | 2/2008 | Bulkes |
| 2008/0046062 A1 | 2/2008 | Camps |
| 2008/0058836 A1 | 3/2008 | Moll |
| 2008/0058891 A1 | 3/2008 | Ben-Haim |
| 2008/0086179 A1 | 4/2008 | Sharma |
| 2008/0132968 A1 | 6/2008 | Starkebaum |
| 2008/0147137 A1 | 6/2008 | Cohen |
| 2008/0154191 A1 | 6/2008 | Gobel |
| 2008/0183238 A1 | 7/2008 | Chen |
| 2008/0195171 A1 | 8/2008 | Sharma |
| 2008/0208355 A1 | 8/2008 | Stack |
| 2009/0012421 A1 | 1/2009 | Bek |
| 2009/0018617 A1 | 1/2009 | Skelton |
| 2009/0018619 A1 | 1/2009 | Skelton |
| 2009/0020406 A1 | 1/2009 | Nirmalakhandan |
| 2009/0030475 A1 | 1/2009 | Brynelsen |
| 2009/0069803 A1 | 3/2009 | Starkebaum |
| 2009/0076498 A1 | 3/2009 | Saadat |
| 2009/0088817 A1 | 4/2009 | Starkebaum |
| 2009/0131993 A1 | 5/2009 | Rousso |

(56) References Cited

U.S. PATENT DOCUMENTS

| | | |
|---|---|---|
| 2009/0132001 A1 | 5/2009 | Soffer |
| 2009/0187223 A1 | 7/2009 | Gross |
| 2009/0192564 A1 | 7/2009 | Armstrong |
| 2009/0204063 A1 | 8/2009 | Policker |
| 2009/0210019 A1 | 8/2009 | Kim |
| 2009/0264951 A1 | 10/2009 | Sharma |
| 2009/0281553 A1 | 11/2009 | Kalloo |
| 2010/0004648 A1 | 1/2010 | Edwards |
| 2010/0010388 A1 | 1/2010 | Panken |
| 2010/0049026 A1 | 2/2010 | Gerber |
| 2010/0057085 A1 | 3/2010 | Holcomb |
| 2010/0069789 A1 | 3/2010 | Hirota |
| 2010/0076345 A1 | 3/2010 | Soffer |
| 2010/0170812 A1 | 7/2010 | Odierno |
| 2010/0198039 A1 | 8/2010 | Towe |
| 2010/0228313 A1 | 9/2010 | Starkebaum |
| 2010/0268495 A1 | 10/2010 | Armstrong |
| 2010/0324432 A1 | 12/2010 | Bjoerling |
| 2010/0324644 A1 | 12/2010 | Levi |
| 2011/0004266 A1 | 1/2011 | Sharma |
| 2011/0034967 A1 | 2/2011 | Chen |
| 2011/0046653 A1 | 2/2011 | Addington |
| 2011/0071589 A1 | 3/2011 | Starkebaum |
| 2011/0213437 A9 | 9/2011 | Armstrong |
| 2011/0224665 A1 | 9/2011 | Crosby |
| 2011/0295335 A1 | 12/2011 | Sharma |
| 2011/0295336 A1 | 12/2011 | Sharma |
| 2011/0301662 A1* | 12/2011 | Bar-Yoseph ......... A61N 1/0514 607/40 |
| 2011/0307023 A1 | 12/2011 | Tweden |
| 2011/0307027 A1 | 12/2011 | Sharma |
| 2011/0307028 A1 | 12/2011 | Sharma |
| 2012/0232610 A1 | 9/2012 | Soffer |
| 2012/0232615 A1* | 9/2012 | Barolat ............. A61N 1/36071 607/46 |
| 2012/0259389 A1 | 10/2012 | Starkebaum |
| 2012/0265103 A1 | 10/2012 | Policker |
| 2012/0277619 A1 | 11/2012 | Starkebaum |
| 2012/0296166 A1 | 11/2012 | Kim |
| 2012/0310317 A1 | 12/2012 | Lund |
| 2013/0030503 A1* | 1/2013 | Yaniv ................ A61N 1/36007 607/62 |
| 2013/0035740 A1 | 2/2013 | Sharma |
| 2013/0072928 A1 | 3/2013 | Schaer |
| 2013/0090551 A1 | 4/2013 | Sharma |
| 2013/0178912 A1 | 7/2013 | Sharma |
| 2013/0218229 A1 | 8/2013 | Sharma |
| 2013/0231660 A1 | 9/2013 | Edwards |
| 2013/0238048 A1 | 9/2013 | Almendinger |
| 2014/0012348 A1 | 1/2014 | Starkebaum |
| 2014/0018657 A1 | 1/2014 | Sharma |
| 2014/0081366 A1 | 3/2014 | Bentley |
| 2014/0088664 A1 | 3/2014 | Sharma |
| 2014/0088666 A1 | 3/2014 | Goetz |
| 2014/0107726 A1 | 4/2014 | Voznesensky |
| 2014/0135886 A1 | 5/2014 | Cook |
| 2014/0194953 A1* | 7/2014 | Slavin ................ A61N 1/375 607/66 |
| 2014/0222106 A1 | 8/2014 | Sharma |
| 2014/0228911 A1 | 8/2014 | Sharma |
| 2014/0243593 A1 | 8/2014 | Goode |
| 2014/0249594 A1 | 9/2014 | Sharma |
| 2014/0364678 A1* | 12/2014 | Harry ................ A61H 23/0263 600/12 |
| 2015/0045786 A1 | 2/2015 | Edwards |
| 2015/0057718 A1 | 2/2015 | Sharma |
| 2015/0094789 A1* | 4/2015 | Janzig ............... A61N 1/3752 607/116 |
| 2015/0119952 A1 | 4/2015 | Sharma |
| 2015/0174416 A1* | 6/2015 | Angara ............ A61N 1/3787 320/108 |
| 2015/0224310 A1 | 8/2015 | Sharma |
| 2015/0360037 A1 | 12/2015 | Hahn |
| 2016/0001071 A1 | 1/2016 | Sharma |
| 2016/0015392 A1 | 1/2016 | Gettman |
| 2016/0045730 A1 | 2/2016 | Kim |
| 2016/0059010 A1 | 3/2016 | Sharma |
| 2017/0197028 A1 | 7/2017 | Goldsmith |
| 2017/0224986 A1 | 8/2017 | Imran |
| 2017/0348049 A1 | 12/2017 | Vrba |
| 2018/0154135 A1 | 6/2018 | Goode |

FOREIGN PATENT DOCUMENTS

| | | |
|---|---|---|
| CN | 102725021 | 10/2012 |
| CN | 105641805 | 6/2016 |
| CN | 105641805 A | 6/2016 |
| EP | 1004330 | 5/2000 |
| EP | 1004330 A1 | 5/2000 |
| WO | 199853878 | 12/1998 |
| WO | 9903532 | 1/1999 |
| WO | 9930776 | 6/1999 |
| WO | 0061223 A1 | 10/2000 |
| WO | 0061224 A1 | 10/2000 |
| WO | 2000061223 | 10/2000 |
| WO | 2000061224 | 10/2000 |
| WO | 0238217 A2 | 5/2002 |
| WO | 0243467 A2 | 6/2002 |
| WO | 2002043467 | 6/2002 |
| WO | 02089655 | 11/2002 |
| WO | 2002100481 A1 | 12/2002 |
| WO | 2005051486 A1 | 9/2005 |
| WO | 2007137026 | 11/2007 |
| WO | 2008117296 A1 | 10/2008 |
| WO | 2009009276 | 1/2009 |
| WO | 2009114008 A1 | 9/2009 |
| WO | 2010027963 | 3/2010 |
| WO | 2010135634 | 11/2010 |
| WO | 2012151449 | 11/2012 |
| WO | 2014032030 | 2/2014 |
| WO | 2015034867 | 3/2015 |
| WO | 2015077425 | 5/2015 |
| WO | 2015077435 | 5/2015 |

OTHER PUBLICATIONS

International Search Report for PCT/US2008/053780, dated Jun. 8, 2009.

Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.

International Search Report for PCT/US2008/056479, dated Aug. 20, 2008.

International Search Report for PCT/US2011/027243, dated Jul. 8, 2011.

Christensen et al., 'Physiologic Specialization at Esophagogastric Junction in Three Species', American Journal of Physiology, vol. 225, No. 6, Dec. 1973, 1265-1270.

Cigaina, Valerio; Long-term Follow-Up of Gastric Stimulation for Obesity: The Mestre 8-Year Experience; Obesity Surgery; 14; 2004; S14-22.

Clarke et al,. 'An Endoscopic Implantable Device Stimulates the LES On-Demand By Remote Control in a Canine Model'; Gastrointestinal Endoscopy, vol. 63, No. 5; 2006, AB103, 759.

Clarke et al., 'An endoscopically implantable device stimulates the lower esophageal sphincter on demand by remote control: a study using a canine model', Endoscopy 2007; 39: 72-76

Ellis, et al., 'The Prevention of Experimentally Induced Reflux by Electrical Stimulation ofthe Distal Esophagus', American Journal of Surgery, vol. 115, Apr. 1968, 482-487.

Gonzalez et al., 'Different Responsiveness of Excitatory and Inhibitory Enteric Motor Neurons in the Human Esophagus to Electrical Field Stimulation and to Nicotine', Am J Physiol Gastrointest Liver Physiol, 287:G299-G306, 2004.

International Search Report for PCT/US12/053576, dated Dec. 24, 2012.

(56) References Cited

OTHER PUBLICATIONS

International Search Report for PCT/U82012/033695, dated Aug. 7, 2012.
International Search Report for PCT/US2012/036408, dated Aug. 17, 2012.
International Search Report for PCT/US2013/056520, dated Apr. 4, 2014.
International Search Report for PCT/US2014/053793, dated Mar. 27, 2015.
International Search Report for PCT/US2014/066578, dated Mar. 19, 2015.
Jameison, GG el al. "Laparoscopic Nissen Fundoplication". Annals of Surgery, vol. 220. No. 2, p. 139 (1994).
Kahrilas et al., 'Impact of Fundoplicalion on Bolus Transit Across Esophagogastric Junction', American Physiological Society, 1998, 1386-1393.
Kamath et al., 'Neurocardiac and Cerebral Responses Evoked By Esophageal Vago-Afferent Stimulation in Humans: Effects of Varying Intensities', Cardiovascular Research, 40 (1998) 591-599.
Kantsevoy et al., 'An Endoscopically Implantable On-Demand Stimulator Is Successful in Increasing Lower Esophageal Sphincter Pressure in a Porcine Model'; Gastrointestinal Endoscopy, vol. 61, No. 5: 2005, A879, 222.
Lund et al., 'Electrical Stimulation of Esophageal Smooth Muscle and Effects of Antagonists', American Journal of Physiology, vol. 217, No. 5, Nov. 1969, 1369-1374.
Sallam et al, 'Feasibility of gastric electrical stimulation by percutaneous endoscopic transgastric electrodes'; Gastrointestinal Endoscopy; vol. 68, No. 4; 2008, 754-759.
Sanmiguel et al, 'Effect of electrical stimulation of the LES on LES pressure in a canine model'; Am J Physiol Gastrointest Live Physiol; 295: 389-394; 2008.
Shellock, Frank G. 'RF Bion Microstimulator' MRISafety.com, http://www.mrisafety.com/SafetyInfov.asp?SafetyInfoID=254, Shellock R & D Services, Inc. and Frank G. Shellock, Ph.D., 4 pages, 2014.
Stein el al., 'Three-dimensional Imaging of the Lower Esophageal Sphincter in Gastroesophageal Reflux Disease,' Annual Meeting of the American Surgical Association, Apr. 11-13, 1991, 374-383.
Tam, WCE et al. "Delivery of radiofrequency energy to the lower esophageal sphincter and gastric cardia inhibits transient oesophageal sphincter relaxations and gastro-oesophageal reflux in patients with reflux disease". Gut, 52(4), 479-785 (2003).
Xing et al, 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.
Xing et al, 'Gastric Electrical Stimulation Significantly Increases Canine Lower Esophageal Sphincter Pressure'; Digestive Diseases and Sciences; vol. 50, No. 8 (Aug. 2005), pp. 1481-1487.
Xing et al., 'Gastric Electrical Stimulation Significantly Increases Canine Lower Esophageal Pressure' Gastroenterology 122: May Issue, A579, 2003. Presented as a poster at Digestive Disease Week in Orlando, FL on Monday, May 19, 2003.
International Search Report for PCT/US2015/061108, dated May 26, 2016.
International Search Report for PCT/US2018/025092, dated Jun. 27, 2018.
International Search Report for PCT/US2019/016923, dated Jun. 7, 2019.

* cited by examiner

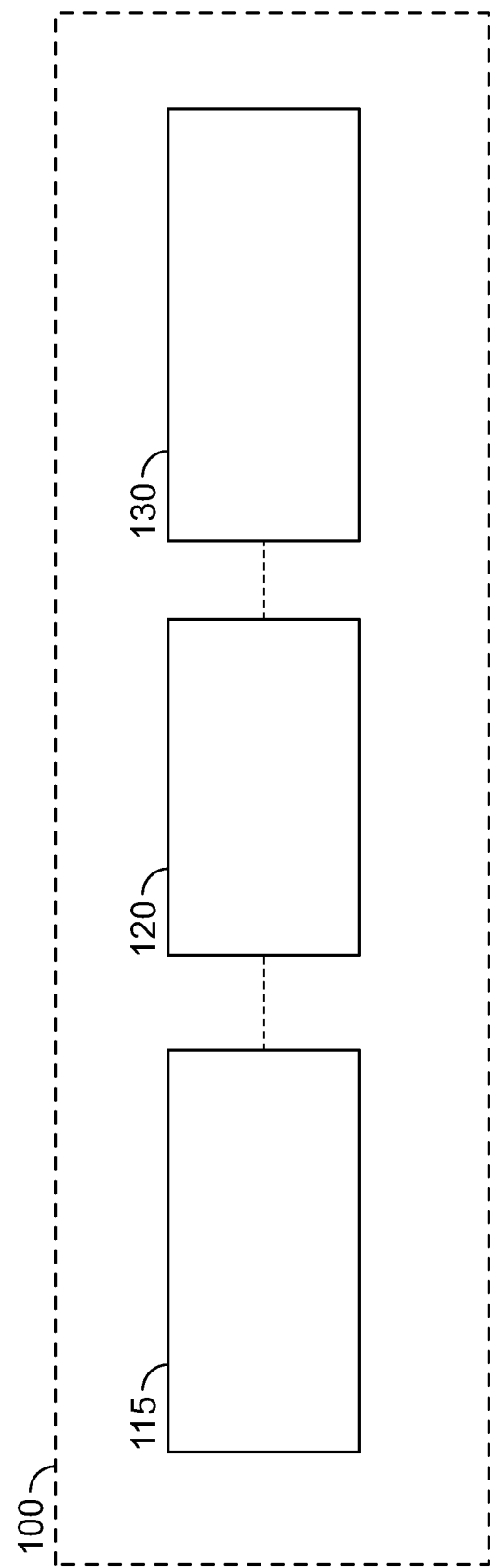

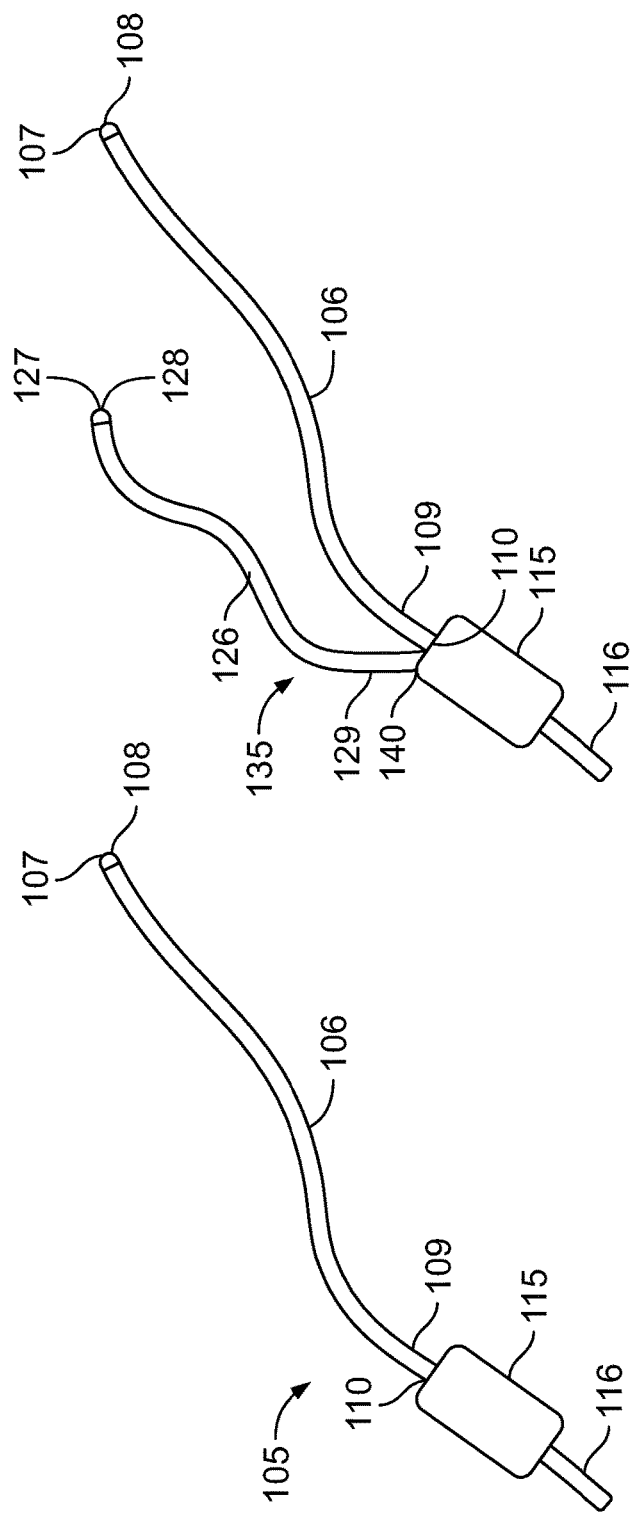
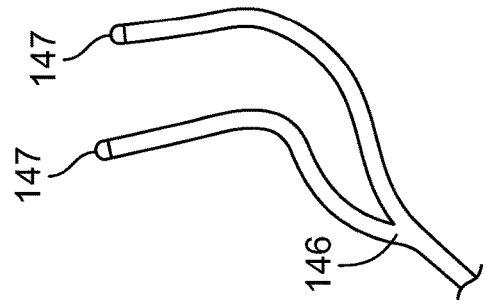
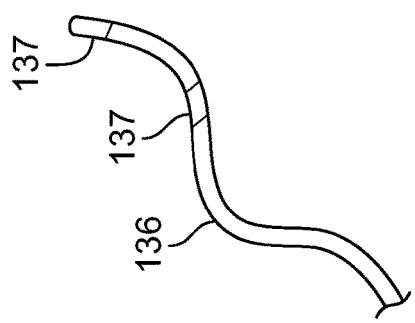

MODULAR STIMULATION SYSTEM FOR THE TREATMENT OF GASTROINTESTINAL DISORDERS

CROSS-REFERENCE

The present application relies on U.S. Provisional Patent Application No. 62/423,334, entitled "Modular Stimulator for the Treatment of Gastrointestinal Disorders" and filed on Nov. 17, 2016, for priority, which is herein incorporated by reference in its entirety.

FIELD OF THE INVENTION

This invention relates generally to a method and system for electrical stimulation of biological systems. More particularly, this invention relates to treating a gastrointestinal condition by using interchangeable modules in a modular stimulator system to efficiently enable a first trial stage and, if successful, a second long term stage of treatment.

BACKGROUND

Gastro-esophageal reflux disease (GERD) is a common problem and is expensive to manage in both primary and secondary care settings. This condition results from exposure of esophageal mucosa to gastric acid and bile as the gastro-duodenal content refluxes from the stomach into the esophagus. The acid and bile damages the esophageal mucosa resulting in heartburn, ulcers, bleeding, and scarring, and long term complications such as Barrett's esophagus (pre-cancerous esophageal lining) and adeno-cancer of the esophagus.

Lifestyle advice and antacid therapy are advocated as first line treatment for the disease. However, since most patients with moderate to severe cases of GERD do not respond adequately to these first-line measures and need further treatment, other alternatives including pharmacological, endoscopic, and surgical treatments are employed.

The most commonly employed pharmacological treatment is daily use of H2 receptor antagonists (H2RAs) or proton-pump inhibitors (PPIs) for acid suppression. Since gastro-esophageal reflux disease usually relapses once drug therapy is discontinued, most patients with the disease, therefore, need long-term drug therapy. However, daily use of PPIs or H2RAs is not universally effective in the relief of GERD symptoms or as maintenance therapy. Additionally, not all patients are comfortable with the concept of having to take daily or intermittent medication for the rest of their lives and many are interested in non-pharmacological options for managing their reflux disease.

Several endoscopic procedures for the treatment of GERD have been tried. These procedures can be divided into three approaches: endoscopic suturing wherein stitches are inserted in the gastric cardia to plicate and strengthen the lower esophageal sphincter, endoscopic application of energy to the lower esophagus, and injection of bulking agents into the muscle layer of the distal esophagus. These procedures, however, are not without their risks, besides being technically demanding and involving a long procedure time. As a result, these procedures have largely been discontinued.

Open surgical or laparoscopic fundoplication is also used to correct the cause of the disease. However, surgical procedures are associated with significant morbidity and small but not insignificant mortality rates. Moreover, long-term follow-up with patients treated by surgery suggests that many patients continue to need acid suppressive medication. There is also no convincing evidence that fundoplication reduces the risk of esophageal adenocarcinoma in the long term.

While electrical stimulation has been, and is being, used to treat GERD, electrical stimulation treatments typically involve positioning and then implanting a pulse generator device using surgical procedures that involve a long procedure time. Moreover, such implantations have to be done without any prior knowledge of whether the patient will therapeutically respond to the stimulation treatment in the long run.

Therefore, these is a need for a modular stimulation system that can be deployed within the patient in a staggered method of treatment. More specifically, it is desirable to have a system comprising a plurality of detachably attachable modules that may be deployed over a first and a second phase of treatment, wherein the first phase of treatment is procedurally rapid, diagnostic in nature, and helps establish an efficacy of the treatment over a short period of therapy. Depending upon the effectiveness or patient response to the first phase of treatment, a second phase, in which a longer term stimulation system is implanted, is then implemented.

It is further desirable to have the patient undergo less invasive medical procedures at the first phase of treatment to assess if the electrical stimulation therapy will at all be useful for the patient.

SUMMARY OF THE INVENTION

The following embodiments and aspects thereof are described and illustrated in conjunction with systems, tools and methods, which are meant to be exemplary and illustrative, not limiting in scope.

The present specification discloses a method for treating a gastrointestinal condition of a patient, comprising the following steps: during a first phase of treatment, placing a microstimulator module within an intra-abdominal space of the patient, wherein said microstimulator module comprises a detachable lead with at least one electrode in electrical communication with a pulse generator; using the microstimulator module, electrically stimulating a treatment site of the patient to provide a therapy using a plurality of pulses generated by said pulse generator; acquiring a plurality of patient response data; assessing an effectiveness of said therapy using the plurality of patient response data; depending on the assessment, initiating a second phase of treatment, wherein the second phase of treatment comprises replacing a portion the microstimulator module with a macrostimulator module by detaching the portion of the microstimulator module from the detachable lead and attaching the macrostimulator module to the detachable lead.

Optionally, said plurality of patient response data comprises at least one of patient symptoms, patient questionnaire responses, patient medication usage, pH levels in the patient's esophagus, impedance-based pH-metry, a manometry value of LES-EEP, esophagitis score, acid exposure events, physiological response, or a presence of Barrett's esophagus.

Optionally, the macrostimulator module comprises a pulse generator and a power source.

Optionally, the microstimulator module comprises a power source that is physically detachable from a remainder of the microstimulator module.

Optionally, said second phase of treatment comprises replacing the power source module with the macrostimulator module. Optionally, said second phase of treatment comprises replacing the power source module and the pulse generator of the microstimulator module with the macrostimulator module, and wherein said macrostimulator module comprises a pulse generator and a power source.

Optionally, the detachable lead of the microstimulator module has a length in a range of 1 cm to 40 cm and a diameter in a range of 0.1 mm to 3 mm.

Optionally, a detachable lead of the macrostimulator module has a length ranging from 1 cm to 100 cm and a diameter ranging from 0.5 mm to 4 mm.

The power source module may be rechargeable or non-rechargeable. Optionally, the power source module has a capacity ranging from 1 mAh to 1000 mAh.

The power source of the macrostimulator module may be rechargeable or non-rechargeable. Optionally, the power source of the macrostimulator module has a capacity ranging from 100 mAh to 5000 mAh.

Optionally, said plurality of pulses are defined by an amperage ranging from 0.1 mA to 10 mA, a frequency ranging from 1 Hz to 100 Hz, a duration ranging from 50 μsec to 1000 μsec, a duty cycle ranging from 1% to 100% and a pulse shape that is monopolar or bipolar.

Optionally, said first phase of treatment is performed for a period of less than 90 days.

Optionally, said second phase of treatment is performed for a period greater than 90 days.

Optionally, the pulse generator of the macrostimulator module generates pulses having an amperage ranging from 0.1 mA to 10 mA, a frequency ranging from 1 Hz to 100 Hz, a duration ranging from 50 μsec to 1000 μsec, a duty cycle ranging from 1% to 100% and a pulse shape that is monopolar or bipolar.

The power source module may be detachably attached to said pulse generator of the microstimulator module through an intermediate lead. Optionally, the power source module is detachably attached directly to said pulse generator of the microstimulator module.

Optionally, said second phase of treatment comprises placing the macrostimulator module in a subcutaneous space or an intra-abdominal space within the patient.

Optionally, during the first phase of treatment, at least one of a treatment site, the amperage of the plurality of pulses, the frequency of the plurality of pulses, the duration of the plurality of pulses, the duty cycle of the plurality of pulses, or the pulse shape of the plurality of pulses is modified at least once.

The present specification also discloses a system for treating a gastrointestinal condition of a patient with a plurality of detachably interconnectable modules, the system comprising: a microstimulator module comprising a pulse generator in electrical communication with a detachable lead and a first power source to stimulate a treatment site; and a macrostimulator module comprising a second power source and a receptacle adapted to place the macrostimulator module in electrical communication with the detachable lead.

Optionally, the first power source is adapted to be detachably attachable to said pulse generator of the microstimulator module.

Optionally, the first power source is adapted to be detachably attachable to the pulse generator of the microstimulator module through an intermediate lead. Optionally, the first power source is detachably attachable directly to the pulse generator of the microstimulator module.

Optionally, the detachable lead has a length in a range of 1 cm to 40 cm and a diameter in a range of 0.1 mm to 3 mm. Optionally, the detachable lead has a length ranging from 1 cm to 100 cm and a diameter ranging from 0.5 mm to 4 mm.

Optionally, the second power source module is rechargeable and has a capacity ranging from 1 milliamp hour (mAh) to 1000 mAh.

Optionally, the first power source module is non-rechargeable and has a capacity ranging from 1 milliamp hour (mAh) to 1000 mAh.

Optionally, the pulse generator of the microstimulator module is adapted to generate pulses with an amperage ranging from 0.1 mA to 10 mA, a frequency ranging from 1 Hz to 100 Hz, a duration ranging from 50 μsec to 1000 μsec, a duty cycle ranging from 1% to 100% and pulse shapes that are either monopolar or bipolar.

Optionally, the macrostimulator module does not have a pulse generator.

Optionally, the macrostimulator module and the microstimulator module are adapted to be implanted within a subcutaneous space of the patient.

Optionally, the macrostimulator module and the microstimulator module are adapted to be implanted within an intra-abdominal space of the patient.

Optionally, the pulse generator of the microstimulator is adapted to be detachably attachable to the macrostimulator module through an intermediate lead.

Optionally, the first power source module is detachably attachable to the pulse generator of the microstimulator module.

Optionally, the macrostimulator is attachable to at least one of the pulse generator of the microstimulator module and the detachable lead.

The present specification also discloses a modular stimulator system having a plurality of detachably attachable or interconnectable modules, adapted for placement at or proximate a patient's treatment site using percutaneous, endoscopic, laparoscopic, or surgical techniques, or any combination thereof, and programmed to treat a gastrointestinal condition such as gastroesophageal reflux disease (GERD). The modular stimulator system comprises a microstimulator module comprising a detachable lead with at least one electrode in electrical communication with a pulse generator to stimulate the treatment site, a small power source module capable of being detachably attachable to the pulse generator of the microstimulator module, and a macrostimulator module, wherein the microstimulator module and the small power source module are deployed within an intragastric, extragastric, or subcutaneous space of the patient during a first phase of treatment, and wherein the macrostimulator module is deployed during a second phase of treatment in a subcutaneous space of the patient.

Optionally, the macrostimulator module comprises a detachable lead with at least one electrode in electrical communication with a pulse generator and a power source, wherein, during the second phase of treatment, the macrostimulator module replaces the microstimulator module and the small power source module.

Optionally, the macrostimulator module comprises a detachable lead in electrical communication with a pulse generator and a power source, wherein, during the second phase of treatment, the macrostimulator module replaces the small power source module. In another embodiment, the macrostimulator module replaces the small power source module and the pulse generator of the microstimulator module during the second phase of treatment.

Optionally, the macrostimulator module comprises a detachable lead in electrical communication with the power source, wherein, during the second phase of treatment, the macrostimulator module replaces the small power source module.

Optionally, the small power source module is detachably attachable to the pulse generator of the microstimulator module either without or through an intermediate lead.

Optionally, the detachable lead of the microstimulator module is 1 cm to 40 cm in length and 0.1 mm to 3 mm in diameter.

Optionally, the detachable lead of the macrostimulator module has a length ranging from 1 cm to 100 cm and a diameter ranging from 0.5 mm to 4 mm.

Optionally, the small power source module is non-rechargeable or rechargeable and has a capacity ranging from 1 milliamp hour (mAh) to 1000 mAh.

Optionally, the power source of the macrostimulator module is non-rechargeable or rechargeable and has a capacity ranging from 100 mAh to 5000 mAh.

Optionally, the pulse generator of the microstimulator module and the macrostimulator module generates pulses with any combination of the following pulse characteristics: amperage ranging from 0.1 mA to 10 mA; frequency ranging from 1 Hz to 100 Hz; duration ranging from 50 μsec to 1000 μsec; duty cycle ranging from 1% to 100%, and pulse shapes of monopolar or bipolar. Pulse sessions are delivered in either an anodic configuration, cathodic configuration, or an alternating anodic/cathodic configuration. In one embodiment, the duration of each stimulation session ranges from 1 minute to 180 minutes and the number of sessions per day ranges from 1 to 24.

Optionally, the first phase of treatment is executed for a period of less than 90 days while the second phase of treatment is executed for a period greater than 90 days.

Optionally, the microstimulator module also comprises an anchoring unit to help anchor it to the treatment/implantation site.

Optionally, the macrostimulator module also comprises a sensor module which senses various physiological parameters or data through one or more sensing electrodes or sensors (e.g., accelerometer) so that the treatment stimulation is initiated or terminated based upon sensed data.

The present specification also discloses a method of treating a gastrointestinal condition, such as gastroesophageal reflux disease (GERD), in a patient using a modular stimulator system. The method comprises placing a microstimulator module detachably attached with a small power source module within an intragastric, extragastric, or subcutaneous space of the patient during a first phase of treatment, wherein the microstimulator module comprises a detachable lead with at least one electrode in electrical communication with a pulse generator; electrically stimulating a treatment site of the patient to provide a therapy using a plurality of pulses generated by the pulse generator; recording/monitoring a plurality of patient response data; assessing effectiveness/efficacy of the therapy using the plurality of patient response data; and, deciding if a second phase of treatment should be implemented, wherein the second phase of treatment involves using a macrostimulator module.

Optionally, the plurality of patient response data comprise the patient's symptoms, increase or decrease in medication need, manometry value of LES-EEP, pH levels in esophagus, acid exposure events, and physiological response.

Optionally, the second phase of treatment comprises replacing the microstimulator module and the small power source module with the macrostimulator module, wherein the macrostimulator module comprises a detachable lead with at least one electrode in electrical communication with a pulse generator and a power source.

Optionally, the second phase of treatment comprises replacing the small power source module with the macrostimulator module, wherein the macrostimulator module comprises a detachable lead in electrical communication with a larger power source.

Optionally, the second phase of treatment comprises replacing the small power source module with the macrostimulator module, wherein the macrostimulator module comprises a detachable lead in electrical communication with a power source.

Optionally, the second phase of treatment comprises replacing the small power source module and the pulse generator of the microstimulator module with the macrostimulator module, wherein the macrostimulator module comprises a detachable lead in electrical communication with a pulse generator and a power source.

Optionally, during the first phase of treatment at least one of a treatment site or a characteristic of the plurality of pulses generated by the pulse generator of the microstimulator module is modified at least once in order to decide implementation of the second phase of treatment.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 1A is a block diagram illustration of one embodiment of a modular stimulator system of the present specification;

FIG. 1B is an illustration of a modular stimulation system in accordance with one embodiment of the present specification;

FIG. 1C is an illustration of a modular stimulation system having two leads in accordance with one embodiment of the present specification;

FIG. 1D is an illustration of a lead with more than one electrode arranged in series in accordance with one embodiment of the present specification;

FIG. 1E is an illustration of a lead with more than one electrode arranged in parallel in accordance with one embodiment of the present specification;

DETAILED DESCRIPTION OF THE INVENTION

Figure 1F:
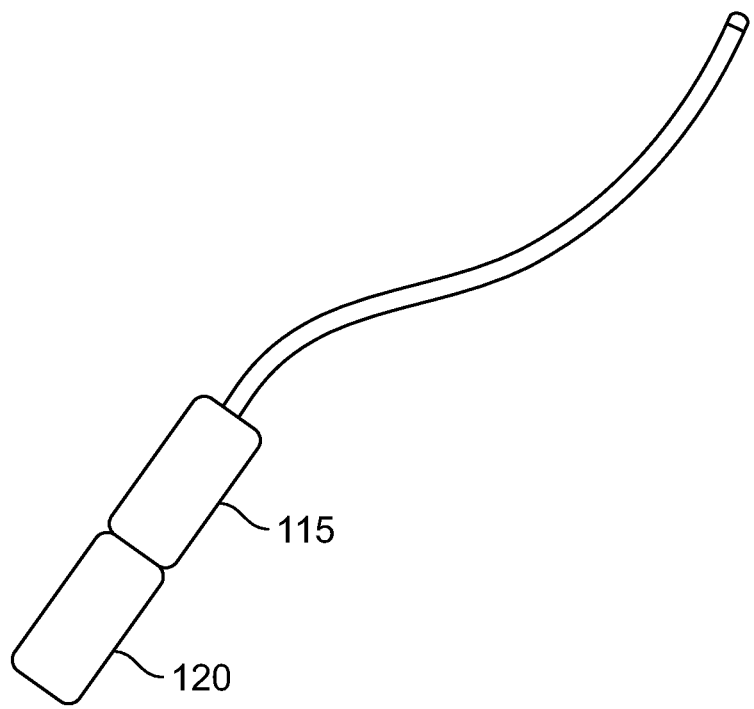
FIG. 1F is an illustration of a small power source module connected to a microstimulator module in accordance with one embodiment of the present specification.

The present specification describes methods and systems for treating gastroesophageal reflux disease (GERD) by implanting a modular stimulator system, in a first and second phase of stimulation treatment, using any conventional surgical, laparoscopic, endoscopic, radiological, stereotactical or other minimally invasive surgical techniques known to persons of ordinary skill in the art. The modular stimulator system comprises a microstimulator, a small power source, and a macrostimulator module that are detachably attachable to each other. In one embodiment, the microstimulator module and the small power source module are combined in one single module. In another embodiment, the microstimulator module and the small power source module comprise two separate modules.

For the first phase of treatment, the microstimulator module and small power source are implanted with a stimulating electrode proximate a target tissue. In various embodiments, the first phase is performed using an endoscopic, percutaneous, or combined endoscopic/percutaneous approach. In some embodiments, the first phase is performed using a percutaneous approach aided by endoscopy. The implantation is performed similarly to a gastric percutaneous endoscopic gastrostomy (PEG) procedure used to place a feeding tube and is performed by a gastroenterologist. The electrodes are placed on the outer surface of the gastric wall or in the gastric wall muscle. The electrodes can reside on the surface of the gastric wall and/or within the gastric wall, but the gastric wall is never penetrated (for surface only electrodes), or never fully penetrated, such that the gastric lumen is not entered. In some embodiments, this approach is used for reflux patients with hiatal hernias <3 cm in length or with no hiatal hernia. Electrical stimulation is provided for a short period of time and treatment efficacy is evaluated through clinical results and patient reporting. If therapy is not effective, stimulation parameters can be changed and/or the implantation site can be moved. If therapy is still not effective, the microstimulator module and small power source are removed and the patient has not been subjected to any significantly invasive procedures.

If therapy is effective, portions of the microstimulator module and/or small power source are replaced minimally invasively with the macrostimulator module for long term therapy of the second phase of treatment. In various embodiments, the second phase is a surgical phase that can be performed using local or general anesthesia with only subcutaneous access. In some embodiments, the macrostimulator module replaces the entire microstimulator module and small power source module, if the two are combined into one single module. In other embodiments, wherein the microstimulator module and small power source module comprise separate modules, the macrostimulator module replaces only the small power source module. It should be appreciated that the methods and systems are being described with respect to specific embodiments, but are not limited thereto.

Components of the modular stimulation system of the present specification include an implantable pulse generator and one or more stimulating electrodes. In various embodiments, the implantable pulse generator and stimulating electrodes are similar to those described in the following: United States Patent Application Publication Number 20030014086A1, filed on Jul. 12, 2002 and now issued as U.S. Pat. No. 6,901,295; United States Patent Application Publication Number 20080086179A1, filed on Oct. 9, 2006 and now issued as U.S. Pat. No. 7,738,961; United States Patent Application Publication Number 20130178912A1 filed on Oct. 26, 2012; United States Patent Application Publication Number 20120265103A1 filed on Apr. 14, 2012; United States Patent Application Publication Number 20090264951A1, filed on Jan. 25, 2009 and now issued as U.S. Pat. No. 8,543,210; United States Patent Application Publication Number 20130035740A1, filed on May 3, 2012 and now issued as U.S. Pat. No. 9,020,597; United States Patent Application Publication Number 20110307027A1, filed on Mar. 4, 2011 and now issued as U.S. Pat. No. 8,712,529; United States Patent Application Publication Number 20110307028A1, filed on Mar. 4, 2011 and now issued as U.S. Pat. No. 8,712,530; United States Patent Application Publication Number 20110295335A1, filed on Mar. 4, 2011 and now issued as U.S. Pat. No. 8,447,403; United States Patent Application Publication Number 20110295336A1, filed on Mar. 4, 2011 and now issued as U.S. Pat. No. 8,447,404; United States Patent Application Publication Number 20090132001A1, filed on Nov. 12, 2008 and now issued as U.S. Pat. No. 8,160,709; United States Patent Application Publication Number 20120232610A1, filed on Mar. 13, 2012 and now issued as U.S. Pat. No. 8,538,534; United States Patent Application Publication Number 20140088664A1, filed on Aug. 23, 2013 and now issued as U.S. Pat. No. 9,623,238; United States Patent Application Publication Number 20140018657A1, filed on Jul. 2, 2013 and now issued as U.S. Pat. No. 8,798,753, all of which are hereby incorporated by reference in their entirety.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

FIG. 1A is a block diagram illustration of a modular stimulator system 100 in accordance with an embodiment of the present specification. In various embodiments, the system 100 provides electrical stimulation treatment to patients and comprises three detachably interconnectable modules: a microstimulator module 115, a small power source module 120 and a macrostimulator module 130. The system 100 is configured to be advantageously deployed in phases such that a first phase of treatment incorporates deploying, within an appropriate implantation site, the microstimulator module 115 along with the small power source module 120 for a short test or trial period of time. The first phase of treatment acts as a diagnostic phase to determine if a patient is responding favorably to the treatment and to predict and decide if the patient will benefit from the treatment in the long run. If the patient is found to respond sufficiently favorably in the first phase, then a second phase of treatment is implemented wherein the macrostimulator module 130 replaces the microstimulator module 115 and/or the small power source module 120, to continue the stimulation treatment for a longer period of time.

The modular stimulator system 100 can be used to achieve a plurality of different therapeutic objectives including, but not limited to: treatment of GERD (gastroesophageal reflux disease); treatment of nocturnal GERD; normalizing a patient's LES (lower esophageal sphincter) function; treatment of hypotensive LES; increase resting or baseline LES pressure; treating a patient to normalize esophageal pH; treating a patient to normalize esophageal pH when in the supine position; treating a patient to prevent damage to the patient's lower esophageal sphincter caused by acid reflux; treatment of supine position induced GERD or nocturnal GERD; treatment of activity-induced GERD or nocturnal GERD; prevention of supine position induced GERD or nocturnal GERD; prevention of activity-induced GERD or nocturnal GERD; treating a patient to mitigate damage to the patient's lower esophageal sphincter caused by acid reflux; treating a patient to stop progression of damage to the patient's lower esophageal sphincter caused by acid reflux; treating a patient to minimize transient relaxations of the patient's lower esophageal sphincter; modifying or increasing LES pressure; modifying or increasing esophageal body pressure; modifying or improving esophageal body function; modifying or improving esophageal sensation induced by the refluxate; modifying or improving the volume of refluxate; modifying or improving the clearance of the refluxate; reducing incidents of heartburn; modifying or improving esophageal acid exposure; increasing lower esophageal tone; detecting when a patient swallows; detecting when a patient is eating; treating a gastrointestinal condition of a patient; treating a patient to minimize the patient's consumption of certain solids or liquids; reducing patient symptoms associated with GERD or nocturnal GERD wherein such reduction is measured by an improvement in a patient quality of life survey and wherein said improvement is calculated by having a patient provide a first set of responses to said quality of life survey prior to treatment and having a patient provide a second set of responses to said quality of life survey after said treatment and comparing the first set of responses to said second set of responses; treatment of gastroparesis; treatment of obesity; treatment of type 2 diabetes; treatment of irritable bowel syndrome; treatment of fecal incontinence; treating a patient for any of the above-listed therapeutic objectives with the additional requirement of avoiding tissue habituation, tissue fatigue, tissue injury or damage, or certain adverse reactions, including, but not limited to, chest pain, difficulty in swallowing, pain associated with swallowing, heartburn, injury to surrounding tissue, or arrhythmias.

The modular stimulator system 100 may be implanted within a plurality of anatomical regions to achieve one or more of the therapeutic objectives described above. Treatment sites, or implantation sites, include: the lower esophageal sphincter (LES); proximate the LES; in the vicinity of the LES; the esophageal body; the upper esophageal sphincter (UES); within, proximate, or in the vicinity of the gastro-esophageal junction; the esophagus, including the esophageal body, LES, and UES; proximate the esophagus; in the vicinity of the esophagus; at or within the stomach, including the gastric wall, the gastric cardia, the gastric fundus, the gastric corpus, the gastric antrum, the gastric lesser curvature, the gastric greater curvature, and the pyloric sphincter, including both the anterior and posterior sides of these gastric sites, wherein the anterior side is preferred; the duodenum; the small bowel; the large bowel; the anal sphincter; proximate nerves supplying the LES or gastro-esophageal junction; proximate nerves supplying the esophageal body; proximate nerves supplying the UES; proximate nerves supplying the esophagus, including the esophageal body, LES, and UES; proximate nerves supplying the stomach, including the gastric wall and pyloric sphincter; proximate nerves supplying the duodenum; proximate nerves supplying the small bowel; proximate nerves supplying the large bowel; or proximate nerves supplying the anal sphincter.

Referring now to FIG. 1B, a modular stimulation system 105 comprises a detachable lead 106 that has one or more electrodes 107 at a distal end 108 and electrical connectors 110 at a proximal end 109 to connect to a microstimulator module 115. The microstimulator module 115 comprises a pulse generator. In another embodiment, shown in FIG. 1C, a modular stimulation system 135 includes two detachable leads 106, 126 that are connected to a microstimulator module 115 using electrical connectors. Each lead 106, 126 has one or more electrodes 107, 127 at a distal end 108, 128 and electrical connectors 110, 140 at a proximal end 109, 129 to connect to a microstimulator module 115. In various embodiments, the detachable lead(s) has a length ranging from 1 cm to 40 cm. In embodiments having leads 136, 146 with more than one electrode, referring to FIGS. 1D and 1E, the electrodes 137, 147 may be in series (in-line) as seen in FIG. 1D or parallel (bifurcated) as seen in FIG. 1E.

In various embodiments, the electrode(s) comprise a conducting ceramic, conducting polymer, and/or a noble or refractory metal, such as gold, silver, platinum, iridium, tantalum, titanium, titanium nitride, niobium, stainless steel, or their alloys, with or without conductive coatings such as iridium oxide, platinum black, titanium nitride, conducting polymers, or any coating designed to reduce electrode-tissue interface impedance and increase charge injection. The objective of this choice of materials is to minimize corrosion, electrolysis, and damage to the surrounding tissues. In one embodiment, the alloy comprising the electrode(s) is a shape memory alloy (SMA) that at body temperature conforms to a pre-designated shape to aid with anchoring or positioning for ideal stimulation. In another embodiment, the electrode is not made up of a shape memory alloy (SMA), but has a pre-configured shape designed to prevent retraction once implanted. For example, in an embodiment, the pre-configured shape is barb-shape. One of ordinary skill in the art would however appreciate that any shape which prevents retraction of the electrode after implantation may be employed for the purpose. In various embodiments, the electrode(s) are 1 mm to 20 mm in length and 0.1 mm to 1 mm in diameter.

The modular stimulation system 105, in one embodiment, also comprises an anchoring unit (not shown) to help anchor the system 105 to any given location in the body for implantation. Examples of the anchoring unit comprise a suture from the lumen of the detachable lead 106, a butterfly tab for suturing, a suture sleeve for suturing, a T-tag for anchoring, and a material (bioresorbable or nonresorbable) for suturing. In another embodiment, the anchoring unit is provided with an attachment, which is designed such that it foreshortens after deployment into the patient's body, thereby pulling the system 105 deeper into the particular site in body or snug with the wall and providing better retention. In another embodiment, the anchoring unit is a coating on the device of a material that promotes tissue in-growth into the material. This material can be synthetic (e.g., porous silicone or EPTFE) or biological (e.g., collagen matrix).

The connector(s) 110 enable the microstimulator module 115 to be connected to the proximal end 109 of the lead(s) so that the microstimulator module 115 is in electrical communication with the one or more electrodes. In one embodiment, wherein the microstimulator module 115 is temporarily connected to the lead(s) through the connector(s) 110, the microstimulator module 115 is detachable or disconnectable from the lead(s). Alternatively, in another embodiment, the microstimulator module 115 may be permanently attached to the lead(s) through an integrated connection.

In one embodiment, the body of the detachable lead(s) of the modular stimulation system is equipped with an anchoring unit (as described above), allowing the microstimulator module 115 to freely float. In one embodiment, the body of the lead itself acts as an anchor. This is enabled by designing the body of the lead with any of the techniques mentioned above.

In another embodiment, anchoring is provided on the microstimulator module 115. This may be achieved by providing a separate anchoring unit that attaches to the microstimulator module 115 or by applying anchoring techniques on the pulse microstimulator module 115 itself. The microstimulator module 115 is configured or programmed to provide electrical stimulation in accordance with a plurality of monophasic or biphasic pulse train treatment patterns. For example, the pulse generator can be programmed to vary any combination of: the number of pulses in a pulse train; the shape of pulses in a pulse train; the interval between pulse train repetitions; the duration of each pulse; the timing and amplitude of pulses in trains; the desired amount of amperage to be provided to the target tissue; and, the desired amount of potential to be provided to the target tissue depending upon the load and the current produced. Further, the electrical stimulus may have any shape necessary to produce the desired therapeutic result, including but not limited to, a square, rectangular, sinusoidal, or saw tooth shape. In accordance with certain embodiments, the stimulation pulses have amperage ranging from 0.1 mA to 10 mA, frequency ranging from 1 Hz to 100 Hz, duration ranging from 50 μsec to 1000 μsec, duty cycle ranging from 1% to 100%, and/or pulse shapes of monopolar or bipolar. Pulse sessions are delivered in either an anodic configuration, cathodic configuration, or an alternating anodic/cathodic configuration. In one embodiment, the duration of each stimulation session ranges from 1 minute to 180 minutes and the number of sessions per day ranges from 1 to 24.

In various embodiments, the microstimulator module 115 is hermetically sealed (in an outer shell made of a biocompatible, hermetically sealed material, such as glass, ceramic, metal or polymers. In various embodiments, the outer shell is constructed of an acid corrosion resistant metal such as platinum, gold, tantalum, titanium, or suitable alloys thereof, or, has a non-hermetic encapsulation (such as by using a Parylene coat and being encapsulated with silicone or epoxy). In one embodiment, the microstimulator module 115 is not required to be hermetically sealed as the microstimulator module 115 does not include an integrated chemically-based power source (e.g., battery). In one embodiment, the microstimulator module 115 further comprises at least one connector 116 for connecting to a power source as described below.

In accordance with one embodiment, as shown in FIG. 1F, the connector(s) (116, as seen in FIG. 1B) enables a small power source module 120 to be temporarily or permanently connected to the microstimulator module 115. In an embodiment wherein the small power source module 120 is temporarily connected to the microstimulator module 115 through the power connector(s) 116, the small power source module 120 is detachable or disconnectable from the microstimulator module 115. Alternatively, in one embodiment, the small power source module 120 is permanently attached to the microstimulator module 115 through an integrated connection. The small power source module 120 comprises a mating receptacle to receive the connector(s) 116.

Figure 1G:
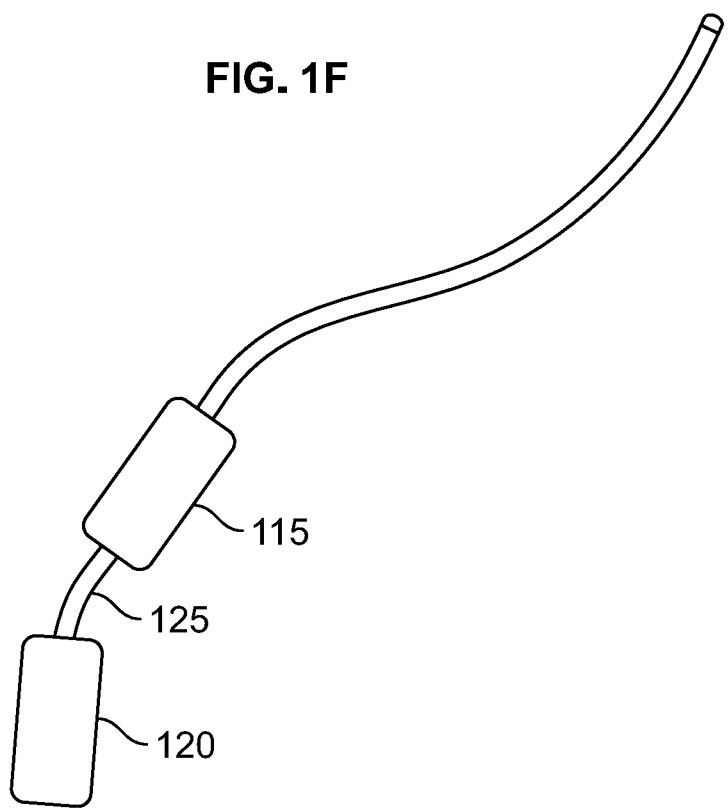
FIG. 1G is an illustration of a small power source module connected to a microstimulator module in accordance with another embodiment of the present specification.

In accordance with another embodiment, as shown in FIG. 1G, the connector(s) enables small power source module 120 to be temporarily or permanently connected to the microstimulator module 115 through an intermediate lead 125. The lead 125, at one end, comprises a receptacle to receive the power connector(s) from the microstimulator module 115 and a connector, at another end, to mate with the receptacle of the small power source module 120.

In one embodiment, the small power source module 120 comprises a self-contained power source with a capacity ranging from 1 milliamp hour (mAh) to 1000 mAh. Examples of such a power source include a primary or non-rechargeable battery, a replenishable or rechargeable battery such as a lithium ion battery or solid-state battery, an electrolytic capacitor, and a super- or ultra-capacitor. In a preferred embodiment, the small power source module 120 comprises a non-rechargeable battery. The power source module 120 may have a hermetic or a non-hermetic encapsulation. In a preferred embodiment, the power source module 120 has a non-hermetic encapsulation such as that of epoxy or silicone thereby reducing the overall cost of the module 120.

In one embodiment, the power source module 120 comprises an antenna and is equipped with the capability to pick up energy transferred wirelessly from outside the body or on the body surface. In one embodiment, any suitable energy transfer technique, such as inductive coupling, RF, MICS, Bluetooth, or Bluetooth LE may be employed with the antenna of the power source module 120. In another embodiment, module 120 is simply an antenna that picks up energy from outside the body. In this embodiment, the module 120 does not include a power source, but makes use of an external energy source that provides power for when therapy delivery is needed. That is, an external energy source is used to power the microstimulator and deliver therapy. This provides an alternative to having a battery within the micro or macrostimulator. In one embodiment, the antenna power source module 120 with external energy source are sufficient to provide the increased energy required in the second phase and the implantation of a macrostimulator is not required. In one embodiment, the external energy source is a wearable device, which may be worn on the body—for example by means of a belt, arm band, wrist band, or ankle strap, or may be adhered to the skin by means of an adhesive. The external energy source may also be embodied in a device carried in the vicinity of the body in which the microstimulator is implanted.

Figure 1H:
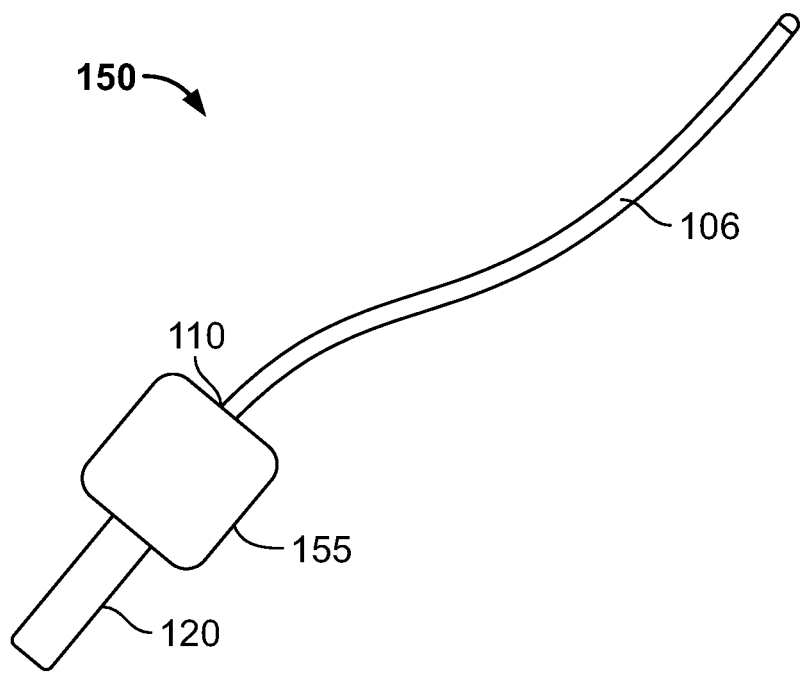
FIG. 1H is a block diagram illustration of one embodiment of a modular stimulator system of the present specification wherein the microstimulator module has been replaced with a macrostimulator module.
Figure 1I:
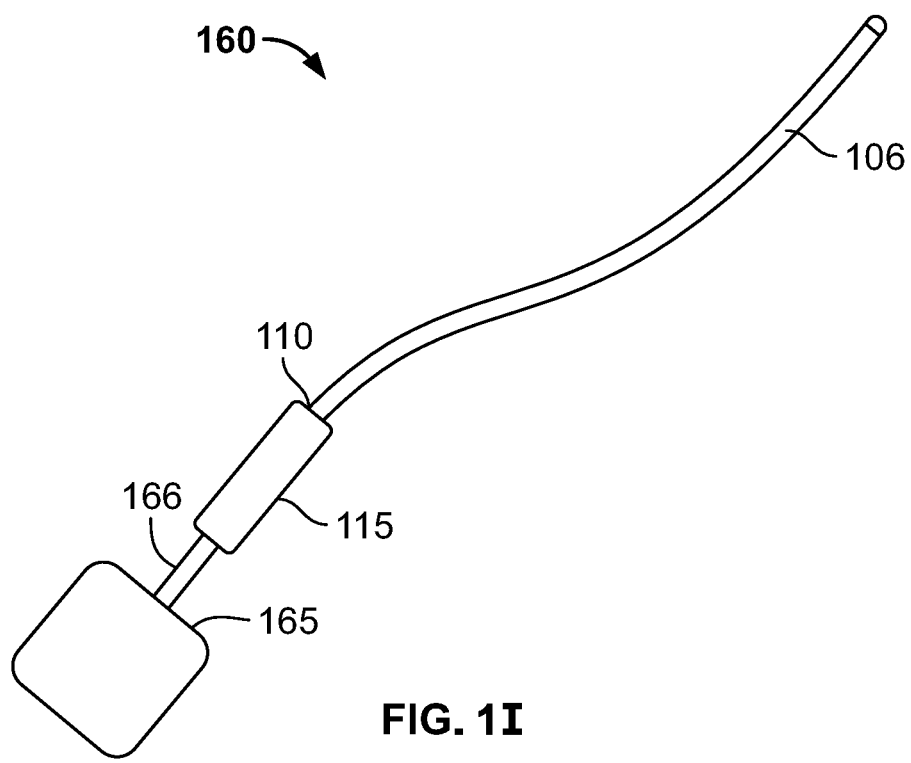
FIG. 1I is a block diagram illustration of one embodiment of a modular stimulator system of the present specification wherein the power module has been replaced with a macrostimulator module.
Figure 1J:
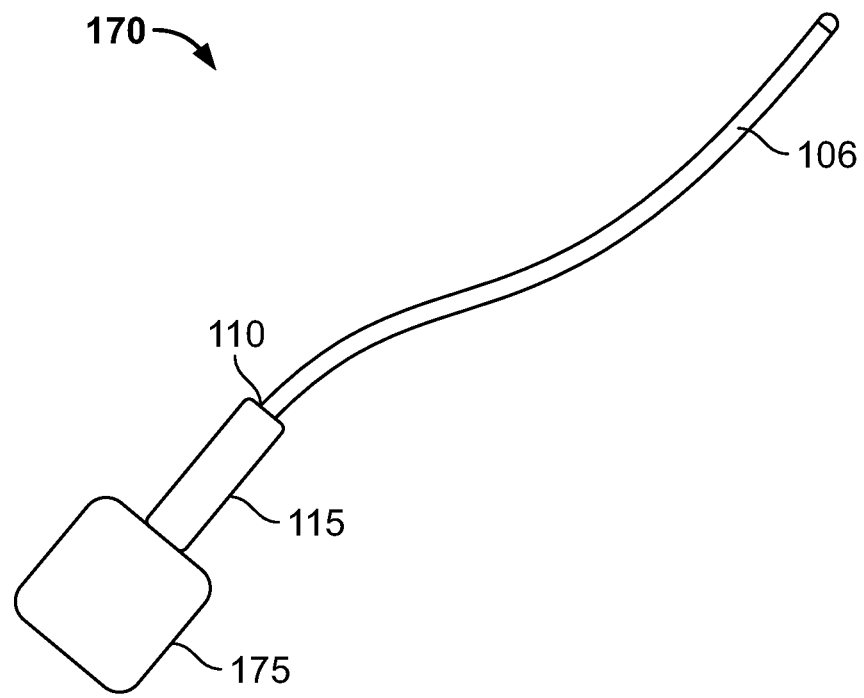
FIG. 1J is a block diagram illustration of another embodiment of a modular stimulator system of the present specification wherein the power module has been replaced with a macrostimulator module.
Figure 1K:
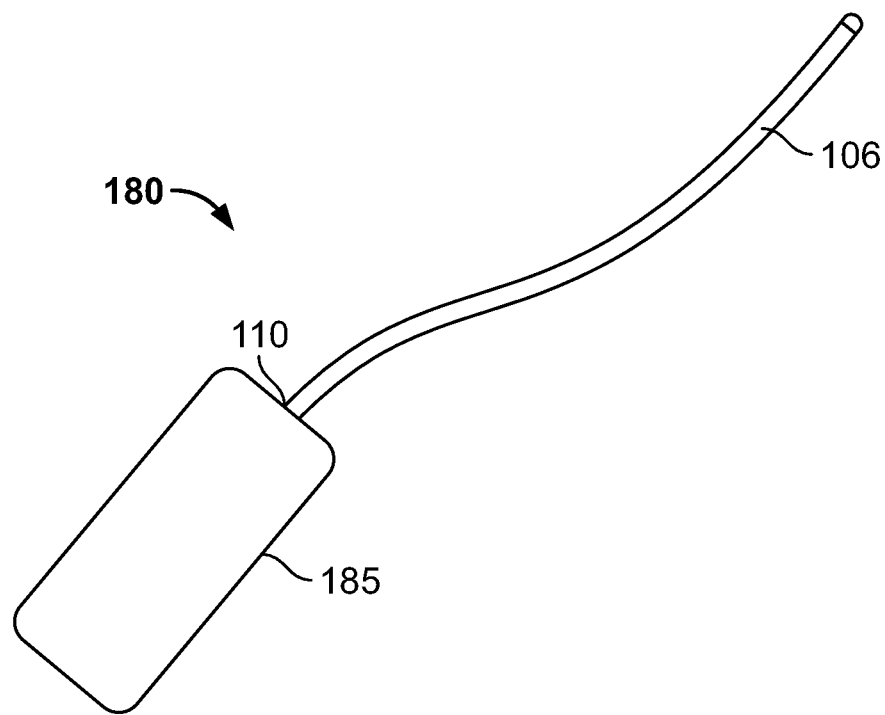
FIG. 1K is a block diagram illustration of one embodiment of a modular stimulator system of the present specification wherein the microstimulator module and power module have been replaced with a macrostimulator module.

FIG. 1H is a block diagram illustration of one embodiment of a modular stimulator system 150 of the present specification wherein the microstimulator module has been replaced with a macrostimulator module 155. A lead 106 is attached via electrical connector 110 to a receptacle on the macrostimulator module 155 and a power source module 120 is attached to said macrostimulator module 155. In some embodiments, the lead 106 is a new lead and is implanted with the macrostimulator module 155 in the procedure when the microstimulator module is replaced with the macrostimulator module. In other embodiments, the lead from the first phase is left at the implantation site and connected, via connector 110, to a receptacle on the macrostimulator module after the macrostimulator module is implanted. FIG. 1I is a block diagram illustration of one embodiment of a modular stimulator system 160 of the present specification wherein the power module has been replaced with a macrostimulator module 165. A connecting lead 166 attached to a receptacle on the macrostimulator 165 connects to the connector (116 in FIG. 1B) of the microstimulator module 115. FIG. 1J is a block diagram illustration of another embodiment of a modular stimulator system 160 of the present specification wherein the power module has been replaced with a macrostimulator module 165. A receptacle on the macrostimulator 175 connects directly to the connector (116 in FIG. 1B) of the microstimulator module 115 and no connecting lead is required. In the embodiments depicted in FIGS. 1I and 1J, the macrostimulator module 165, 175 enhances the function of the microstimulator module 115. FIG. 1K is a block diagram illustration of one embodiment of a modular stimulator system 180 of the present specification wherein the both microstimulator module and power module have been replaced with a macrostimulator module 185. A lead 106 is attached via electrical connector 110 to a receptacle on the macrostimulator 185. In this embodiment, the macrostimulator 185 includes its own power source and so the power module is not required.

Referring to FIGS. 1A and 1I simultaneously, the macrostimulator module 130, 165 comprises an implantable stimulator device with a detachable connecting lead 166 and having a form factor comparable to a conventional cardiac pacemaker or neurostimulator. In one embodiment, the detachable connecting lead 166 has a receptacle, at a distal end, to receive and mate with the connector(s) 116 on the macrostimulator module 165. In various embodiments, the connecting lead has a length ranging from 1 cm to 100 cm and a diameter ranging from 0.5 mm to 4 mm. Thus, in one embodiment, the macrostimulator module 130 is configured as an 'integrated stimulator device', comprising: a detachable connecting lead that, at its distal end, has a receptacle to receive and mate with the connector(s) 116; an energy/power source; and, a pulse generator in electrical communication with the lead and energy source.

In various embodiments, the pulse generator of the macrostimulator modules is configured or programmed to electrically stimulate the patient's target tissue in accordance with a plurality of monophasic or biphasic pulse train treatment patterns. For example, in various embodiments, the pulse generator can be programmed to vary any combination of: the number of pulses in a pulse train; the shape of pulses in a pulse train; the interval between pulse train repetitions; the duration of each pulse; the timing and amplitude of pulses in trains; the desired amount of amperage to be provided to the target tissue; and, the desired amount of potential to be provided to the target tissue depending upon the load and the current produced. Further, in various embodiments, the electrical stimulus has any shape necessary to produce the desired therapeutic result, including but not limited to, a square, rectangular, sinusoidal, or saw tooth shape. In accordance with certain embodiments, the stimulation pulses have amperage ranging from 0.1 mA to 10 mA; frequency ranging from 1 Hz to 100 Hz; duration ranging from 50 μsec to 1000 μsec, duty cycle ranging from 1% to 100%, and/or pulse shapes of monopolar or bipolar. Pulse sessions are delivered in either an anodic configuration, cathodic configuration, or an alternating anodic/cathodic configuration. In one embodiment, the duration of each stimulation session ranges from 1 minute to 180 minutes and the number of sessions per day ranges from 1 to 24.

In one embodiment, the macrostimulator module 130 also comprises a sensor module which senses various physiological parameters or data through one or more sensing electrodes or sensors (e.g., accelerometer) so that the treatment stimulation is initiated or terminated based upon sensed data. The sensed data may comprise any one or more of various kinds of physiological stimuli, including, but not limited to, esophageal peristalsis, esophageal pH, esophageal impedance, esophageal pressure, esophageal electrical activity, LES pressure, LES electrical activity, gastric peristalsis, gastric electrical activity, gastric chemical activity, gastric hormonal activity, gastric temperature, gastric pressure, gastric impedance, gastric pH, duodenal peristalsis, duodenal electrical activity, duodenal chemical activity, duodenal hormonal activity, duodenal temperature, duodenal pressure, duodenal impedance, duodenal pH, blood chemical and/or hormonal activity, vagal or other gastrointestinal neural activity and salivary chemical activity, biliary pressure, biliary electrical activity, biliary chemical activity, pancreatic pressure, pancreatic electrical activity, pancreatic chemical activity, pancreatic sphincter pressure, pancreatic sphincter electrical activity, biliary sphincter pressure, biliary sphincter electrical activity, mesenteric vascular pressure, mesenteric vascular flow, and mesenteric vascular chemical contents.

In various embodiments, the stimulating and sensing electrodes are comprised of a conducting ceramic, conducting polymer, and/or a noble or refractory metal, such as gold, silver, platinum, iridium, tantalum, titanium, titanium nitride, niobium, stainless steel, or their alloys, with or without conductive coatings such as iridium oxide, platinum black, titanium nitride, conducting polymers, or any coating designed to reduce electrode-tissue interface impedance and increase charge injection. The objective of this choice of materials is to minimize corrosion, electrolysis, and damage to the surrounding tissues. In one embodiment, the alloy constituting the simulating and sensing electrodes are comprised of a shape memory alloy (SMA) that at body temperature conforms to a pre-designated shape to aid with anchoring or positioning for ideal stimulation.

In another embodiment, the macrostimulator module 130 is configured as a 'lean stimulator device' comprising a detachable connecting lead having, at its distal end, a receptacle to receive and mate with the connector(s) 116, and an energy source. In accordance with various embodiments, the lead has a length ranging from 1 cm to 100 cm and a diameter ranging from 0.5 mm to 4 mm.

In other embodiments, referring to FIGS. 1H and 1J, the macrostimulator module does not comprise a connecting lead, but is only equipped with a receptacle to mate with the connector(s) 110, 140 of leads 106, 126 as seen in FIGS. 1B and 1C. In doing so, in various embodiments, the macrostimulator module replaces the microstimulator module 115 or both the microstimulator module 115 and small power source module 120, shown in FIGS. 1F and 1G.

In one embodiment, the energy source of the macrostimulator module 130 comprises a self-contained power source with a capacity ranging from 100 mAh to 5000 mAh. Examples of such a power source include a primary battery or non-rechargeable battery, a replenishable or rechargeable battery such as a lithium ion battery or solid-state battery, an electrolytic capacitor, and a super- or ultra-capacitor, etc. In various embodiments, wherein the self-contained power source is replenishable or rechargeable, any suitable means of replenishing or recharging the power source may be used, such as an RF link, an optical link, a thermal link, or any other energy-coupling link. In a preferred embodiment, the energy source is replenishable. Persons of ordinary skill in the art would appreciate that use of a non-rechargeable power source would, however, make the macrostimulator more cost-effective compared to using a rechargeable power source.

Referring again to FIG. 1A, in accordance with an aspect of the present specification, the modular stimulator system 100 assesses if a patient may therapeutically benefit from electrical stimulation treatment by temporarily stimulating the patient in a first phase of treatment for a short test/trial period of time, such as less than one week or for a period ranging from 7 to 90 days. The microstimulator module 115 and the small power source module 120 are connected together, in accordance with the embodiment of FIG. 1F or the embodiment of FIG. 1G, and placed in an extragastric space within the patient to provide a first phase of temporary, diagnostic, trial or test treatment for the short period of time.

Figure 2A:
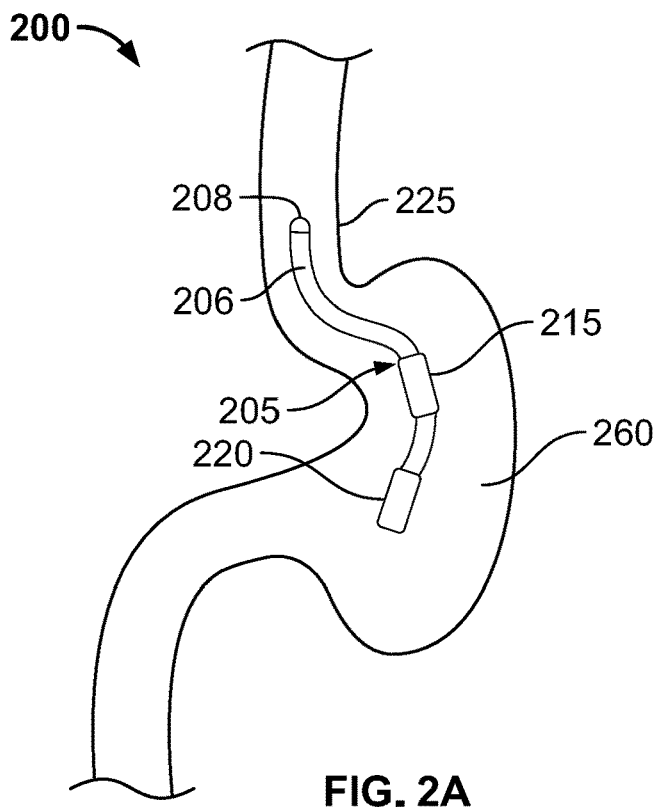
FIG. 2A is an illustration of a gastrointestinal tract with a microstimulator module and a small power source module implanted in accordance with one embodiment of the present specification.

FIG. 2A illustrates a gastrointestinal tract 200 wherein a modular stimulation system 205, comprising a microstimulator module 215 (having a pulse generator) and a small power source module 220 have been implanted (for example, in accordance with the embodiment of FIG. 1G) such that one or more stimulation electrodes, at the distal end 208 of the lead 206, are placed proximate the LES 225, with or without anchoring. In some embodiments, as shown in FIG. 2A, the microstimulator module 215 and the connected small power source module 220 reside on the outer surface of the stomach 260. In other embodiments, the microstimulator module 215 and the connected small power source module 220 reside in the muscle wall of the gastric muscle. In still other embodiments, the microstimulator module 215 and the connected small power source module 220 reside in the intra-gastric space. It should be noted that the microstimulator module 215 and the small power source module 220 can be implanted using any conventional surgical, laparoscopic, endoscopic, radiological, stereotactical or other minimally invasive surgical techniques known to persons of ordinary skill in the art.

Post implantation, in the first phase of treatment, the microstimulator module 215 electrically stimulates the LES 225 in accordance with a plurality of monophasic or biphasic pulse train treatment patterns. In various embodiments, the first phase of stimulation treatment ranges for a short test/trial period of time, such as less than one week or for a period ranging from 7 to 90 days, during which a plurality of patient response data such as, but not limited to, the patient's symptoms, increase or decrease in medication need, manometry value of LES-EEP, pH levels in the esophagus, acid exposure events, and physiological response are recorded. The first phase stimulation treatment data is used to evaluate the efficacy of the stimulation treatment. The treatment data is also used to determine the likely timings of GERD events and the required stimulation parameters to proactively normalize the patient's LES in advance of the GERD event. It should be noted that during the first phase of treatment and based on the stimulation treatment data any one or a combination of the following steps are taken to improve and/or establish the effectiveness of the stimulation treatment: modifying the stimulation pulse train patterns; and, changing the anatomical location site of the stimulation electrode(s). In one embodiment, wherein the patient is found to not at all benefit from the stimulation treatment regimen or if the patient is found to only slightly benefit, the degree of which is not enough to warrant a similar, long term stimulation treatment, then it is decided that the treatment is not working or effective enough for the patient. As a result, the implanted microstimulator module 215 and the small power source module 220 are removed, such as endoscopically, or may alternatively be left in the body for later removal.

Thus, depending upon the extent of benefit derived by the patient and based upon a plurality of monitored patient response data, a decision is made regarding whether the patient would therapeutically benefit from a more permanent and longer duration based second phase of stimulation treatment. Such data can include patient symptoms, patient questionnaire responses, patient medication usage, pH levels in the esophagus including pH-metry, impedance-based pH-metry, manometry value of LES-EEP, endoscopy, esophagitis score, acid exposure events, physiological response, and/or presence of Barrett's esophagus. The managing physician should exercise sound medical judgment when selecting and evaluating any of these metrics.

If it is determined that the patient sufficiently benefits from the first phase of stimulation treatment, then the patient is provided with a second phase of more permanent treatment for a longer period of time, which is typically for more than 90 days and may go up to many years.

Referring now to FIGS. 1A through 1J simultaneously, during the second phase of stimulation treatment the microstimulation module 115 and/or the small power source module 120 are exchanged with the macrostimulator module 130. In one embodiment, only the small power source module 120 is removed, such as percutaneously, endoscopically, or laparoscopically, and replaced with the macrostimulator module 130. In this embodiment, the macrostimulator module 130 is configured as a 'lean stimulator device' with a receptacle to receive and mate with the connector(s) 116 (and therefore attach/connect to the microstimulator module 115 implanted during the first phase of treatment), thereby essentially replacing the small capacity battery of module 120 with a battery of higher capacity/longer work life which may be non-rechargeable or rechargeable. Alternatively, in another embodiment, the macrostimulator module 130 is configured as an 'integrated stimulator device' having a receptacle to receive and mate with the connector(s) 116 (and therefore attach/connect to the microstimulator module 115 implanted during the first phase of treatment), thereby enhancing the stimulation functional capability of the implant (due to the addition of a functionally more enhanced pulse generator of the 'integrated stimulator device') besides adding a battery of higher capacity/longer work life which may be non-rechargeable or rechargeable.

In another embodiment, both the microstimulator module 105 and the small power source module 120 are removed and replaced with the macrostimulator module 130. In this embodiment, the macrostimulator module 130 is configured as the 'integrated stimulator device'.

In still another embodiment, the microstimulator module 115 and the small power source module 120 are removed, keeping the lead 106 and electrode(s) located at the implantation site of the first phase of treatment. The pulse generator 115 and the small power source module 120 are replaced with the macrostimulator module 130. In this embodiment, the macrostimulator module 130 is configured as the 'integrated stimulator device' with a receptacle to receive and mate with the connector(s) 110.

The macrostimulator module 130 is adapted to be implanted in a subcutaneous space, preferably in the abdomen, but any torso location will suffice. It can also be adapted to be implanted in the intra-abdominal cavity.

It may be noted that the microstimulator when implanted occupies a smaller volume in the patient's body as compared to the macrostimulator module, which allows for easy implantation and movement of the microstimulator. In one embodiment, for example, the total length of the microstimulator unit when implanted is in the range of 1-40 mm, whereas the total length of the macrostimulator unit when implanted is in the range of 40-100 mm. In one embodiment, the macrostimulator occupies a volume that is 50-500 percent larger than that occupied by the microstimulator. However, the microstimulator cannot be employed for long term therapy, since its battery life is limited on account of the small power source. As mentioned in the specification, the small power source module of the microstimulator has a capacity ranging from 1 mAh to 1000 mAh, while the power source of the macrostimulator module has a capacity ranging from 100 mAh to 5000 mAh. A larger power source also enables the macrostimulator to deliver stimulation pulses of higher energy. In one embodiment for example, the stimulation pulses delivered by the macrostimulator have 1-100 times more energy than those delivered by the microstimulator. Further, in one embodiment, the macrostimulator is also equipped with a more powerful pulse generator as compared to the microstimulator. Thus, even though the macrostimulator occupies a larger volume compared to the microstimulator, which makes it more difficult to implant and less easily maneuverable, the macrostimulator has the power to sustain stimulation in the long term and is more suitable for deployment in the second phase of treatment, when the effectiveness of stimulation therapy for the patient is established.

Figure 2B:
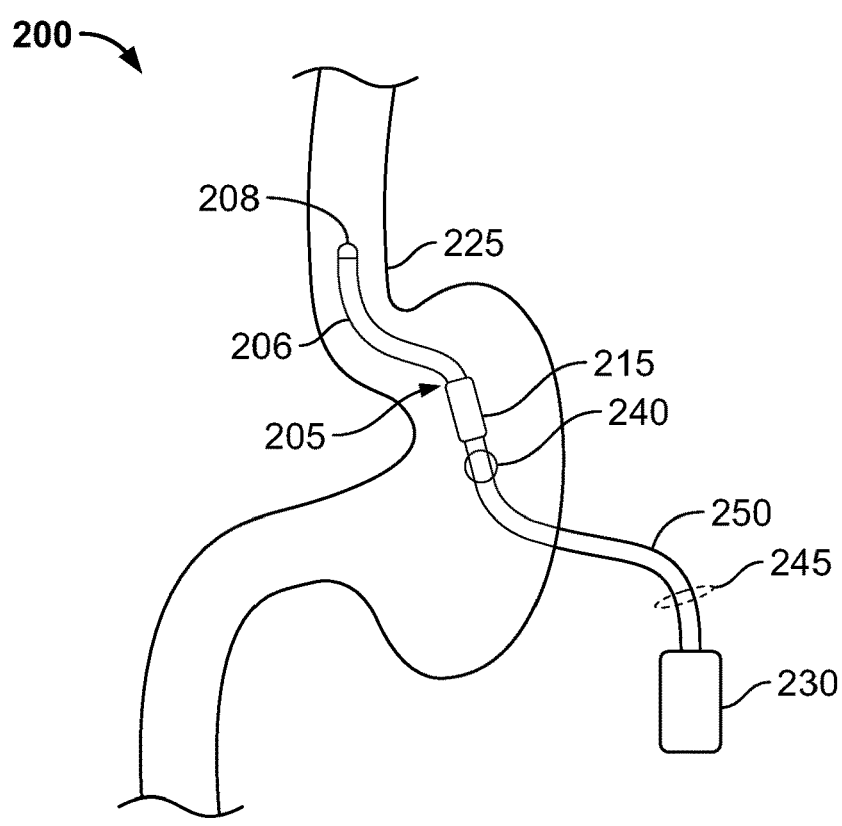
FIG. 2B is an illustration of a gastrointestinal tract with a macrostimulator module deployed in accordance with one embodiment of the present specification.

FIG. 2B illustrates a gastrointestinal tract 200 wherein, as part of the second phase of treatment, the small power source module 220 (shown in FIG. 2A) has been removed, such as endoscopically, and replaced with a macrostimulator module 230. In this illustration, the macrostimulator module 230 is configured as an 'integrated stimulator device' with a connecting lead 250 having a receptacle (but no electrode(s)) to connect/mate with the microstimulator module 215 of the modular stimulation system 205 implanted during the first phase of treatment. In accordance with an exemplary deployment, after disconnecting and removing the small power source module 220 (shown in FIG. 2A) endoscopically, the macrostimulator module 230 is passed, optionally over a catheter, through the channel of an endoscope or laparoscope or alongside an endoscope over a guide-wire or over an attached track or an external channel to the anatomical site of deployment. While the one or more stimulation electrodes at the distal end 208 of the lead 206 remain proximate the LES 225 (in accordance with the implantation during the first phase of treatment of FIG. 2A), a gastric wall perforation 240 (enabling a passageway from an intragastric to an extragastric space) and an abdominal wall perforation 245 (enabling a passageway from an intraabdominal cavity to a subcutaneous space) allow the macrostimulator module 230 to be placed between the mucosal and serosal layers of the stomach wall. In one embodiment, the perforations 240, 245 are made using a catheter needle that allows for the making of minimal incisions. The lead 250 is connected with the existing microstimulator module 215.

Thus, it should be appreciated by those skilled in the art that the phased deployment of the modules of the modular stimulation system of the present specification and the resultant phased method of treatment provides for predicting the patient's likely physiological response to permanent/long-term stimulation. Also, using the microstimulator module and the small power source module, which together constitute a fairly small form factor, in the first phase of treatment requires less invasive medical procedures to be performed on the patient at the beginning, before it is known whether or not the electrical stimulation therapy will work for the patient. Less invasive procedures also allow the microstimulator module deployed in the initial phase of therapy to be easily removed, without the need for advanced surgery, in case stimulation therapy proves ineffective for the patient. Alternately, if the therapy shows promising results in the initial phase for the patient, stimulation may be enhanced or made to continue for a longer period if required, by simply replacing the microstimulator module or the power source module deployed in the first phase, with a macrostimulator. The replacement/enhancement procedure is also minimally invasive, and may be performed only requiring access to the subcutaneous space, for example.

Figure 3:
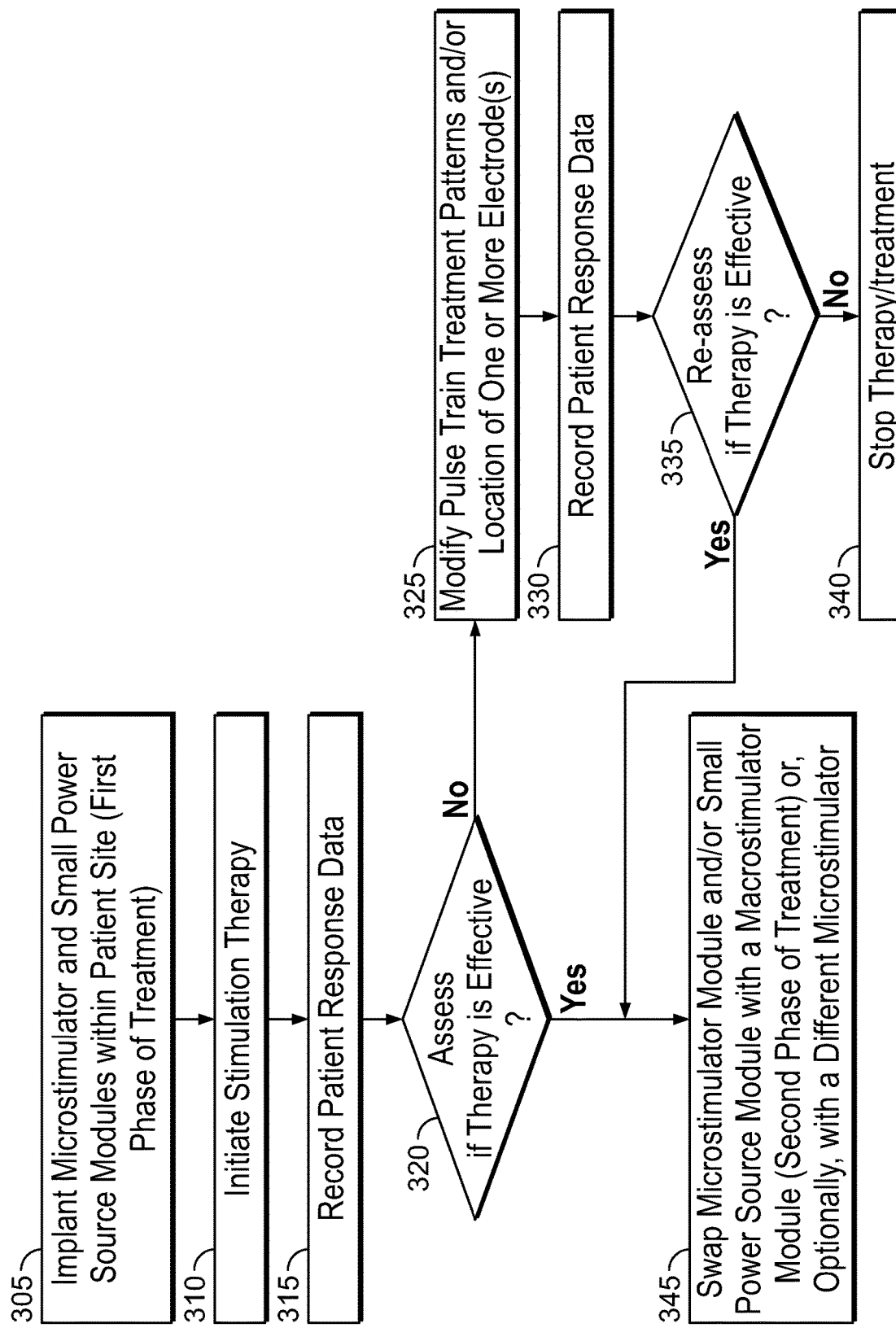
FIG. 3 is a flowchart illustrating an exemplary phased method of employing a modular stimulation system of the present specification and, FIG. 4 is a flowchart illustrating a preferred embodiment of using the modular system of the present specification.

FIG. 3 is a flowchart illustrating an exemplary phased method of employing the modular stimulation system 100 of FIG. 1A in a patient with gastroesophageal reflux disease (GERD). In a first phase of treatment, at step 305, a microstimulator module interconnected with a small power source module is placed, such as endoscopically, within an intragastric space of a patient so that one or more stimulating electrodes connected to the microstimulator module are located proximate the lower esophageal sphincter (LES). Diagnostic stimulation therapy for the patient is then initiated at step 310 by having a pulse generator of the microstimulator module provide electrical stimulation in accordance with a plurality of monophasic or biphasic pulse train treatment patterns. At a therapeutically acceptable duration after initiation of the therapy, a plurality of diagnostic patient response data is recorded/monitored at step 315 to assess, at step 320, the efficacy of the stimulation therapy. The diagnostic patient response data includes data such as, but not limited to, the patient's symptoms, increase or decrease in medication need, patient questionnaire responses, manometry value of LES-EEP, pH levels in the esophagus including pH-metry and impedance-based pH-metry, endoscopy, esophagitis score, acid exposure events, presence of Barrett's esophagus, and physiological response.

If the diagnostic patient response data indicates that the therapy/treatment has not been sufficiently effective (that is, not at all effective or less than an acceptable degree of effectiveness), then at step 325 the pulse train treatment patterns are modified and/or the location of the one or more electrodes is changed. Patient response data is again recorded/monitored at step 330 and reassessed at step 335.

If the re-recorded patient response data still indicates inadequate efficacy of the treatment then the therapy is stopped at step 340 and the microstimulator module and the small power source module are removed from the patient. In an alternate embodiment, the microstimulator module and the small power source module are left dormant for removal later. Steps 325 and 330 may be required to be implemented more than once, in various embodiments, depending upon the patient response and commensurate decision of the caregiver.

If at the assessment step 320 or at the reassessment step 335, the patient response data indicates that the therapy/treatment has been acceptably effective then a second phase of treatment is implemented. At step 345, the microstimulator module or the small power source module is replaced, such as endoscopically, with a macrostimulator module. In another example, at step 345, the microstimulator module and the small power source module are replaced with the macrostimulator module. The macrostimulator module used for replacement can be configured as a 'lean stimulator device' or as an 'integrated stimulator device' in different embodiments of deployment. Optionally, in one embodiment, the microstimulator module is replaced with another, different microstimulator.

Figure 4:
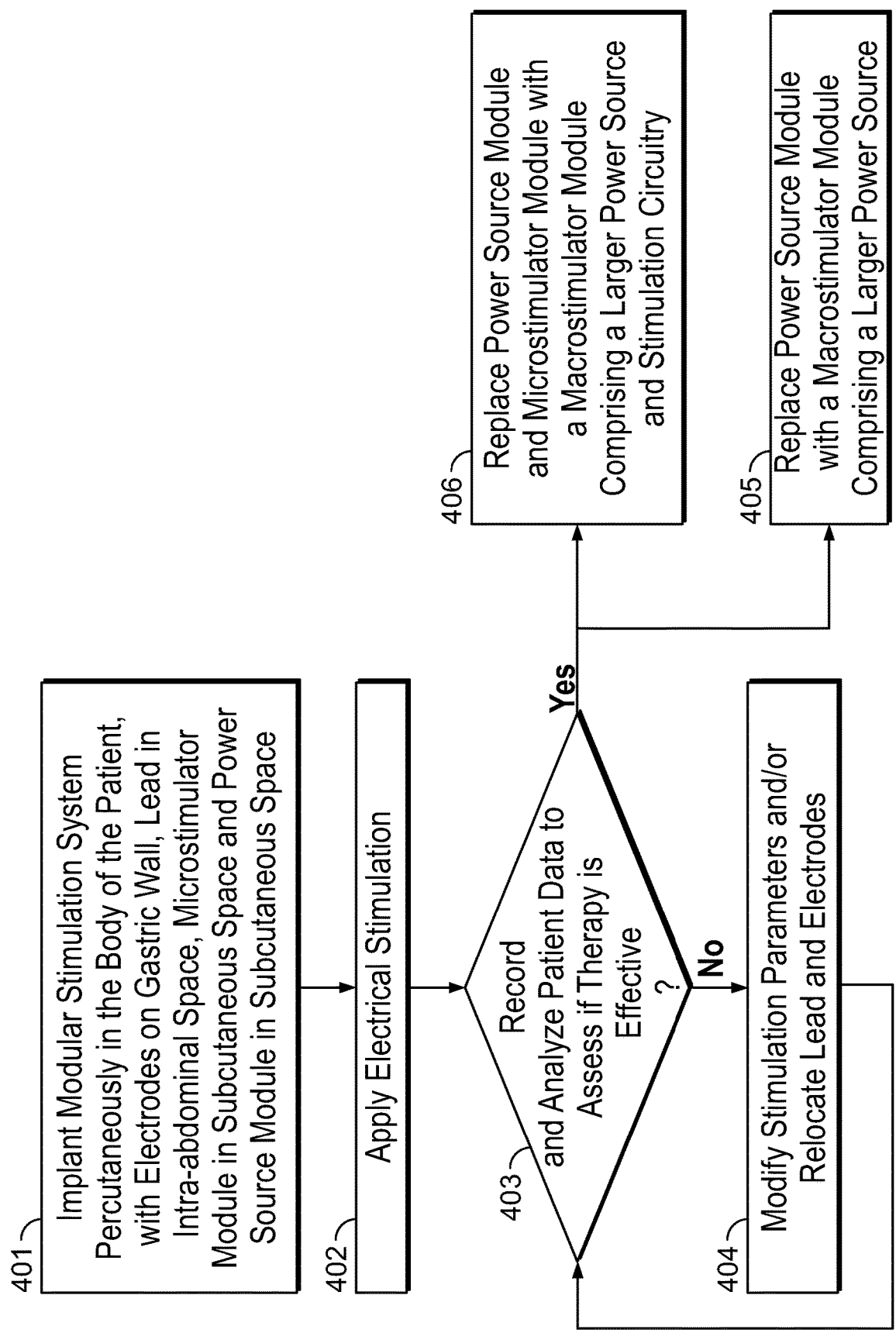

FIG. 4 is a flowchart illustrating a preferred embodiment for using a modular stimulation system of the present specification. Referring to FIG. 4, in the first step 401, a modular stimulation system is implanted percutaneously in the body of the patient. In a preferred embodiment, the implanted components of the system include at least one electrode, at least one lead, a microstimulator and a power source module. In one embodiment, the at least one electrode is implanted in the gastric muscle wall. Alternatively, in a preferred embodiment, the electrodes are placed on the surface of the gastric muscle wall. In one embodiment, the location of the electrodes is preferably on the anterior gastric wall. In a preferred embodiment, the lead is implanted in the intra-abdominal space. The microstimulator is implanted in the intra-abdominal space or the subcutaneous space. In one embodiment, the latter is preferred. The power source module is implanted in the intra-abdominal space or the subcutaneous space, the latter being preferred.

At step 402, electrical stimulation is applied to the patient. The stimulation parameters may include the ranges described in the present specification. In the next step 403, patient data is recorded and analyzed to assess if therapy is effective. Patient data includes, but is not limited to, the patient's symptoms, increase or decrease in medication need, patient questionnaire responses, manometry value of LES-EEP, pH levels in the esophagus including pH-metry and impedance-based pH-metry, endoscopy, esophagitis score, acid exposure events, presence of Barrett's esophagus, and physiological response.

In case patient data indicates a sub-optimal therapeutic response, the stimulation parameters are modified and/or the at least one lead and/or at least one electrode of the stimulation system are relocated in order to achieve an improved response, as shown in step 404. In some embodiments, the amperage of the plurality of pulses, the frequency of the plurality of pulses, the duration of the plurality of pulses, the duty cycle of the plurality of pulses, or the pulse shape of the plurality of pulses is modified at least once.

If a desired therapeutic response is achieved, the power source module is replaced with a macrostimulator module at step 405. The macrostimulator module comprises a larger power source, such as a battery, and a connector or receptacle that connects with the already implanted microstimulator. The macrostimulator module in this case does not have stimulation electronics or a pulse generator. In a preferred embodiment, the macrostimulator module resides in the subcutaneous space. In an alternate embodiment, the macrostimulator module resides in the intra-abdominal space.

Optionally, the microstimulator module and the power source module, are replaced by a macrostimulator module in step 406. In this case, the macrostimulator module comprises stimulation circuitry, a larger power source, such as a battery, and a connector or receptacle that connects with the lead of the stimulation system that remains implanted. In a preferred embodiment, the macrostimulator module resides in the subcutaneous space. In an alternate embodiment, the macrostimulator module resides in the intra-abdominal space.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method for treating a gastrointestinal condition of a patient, wherein the gastrointestinal condition comprises gastroesophageal reflux disease, comprising the following steps:
   during a first phase of treatment, implanting a microstimulator module at a first anatomical location within the patient's gastrointestinal tract, wherein said microstimulator module comprises: at least a pulse generator, a power source module, and a detachable lead, wherein the pulse generator is detachably coupled with the power source module and the detachable lead comprises at least one electrode in electrical communication with the pulse generator that is positioned at a stimulation site;
   using the microstimulator module, electrically stimulating a treatment site of the patient to provide a therapy for gastroesophageal reflux disease using a plurality of pulses generated by said pulse generator; wherein the at least one electrode is in electrical communication with the treatment site;
   acquiring a plurality of patient response data related to the patient's gastroesophageal reflux disease;
   assessing an effectiveness of said therapy using the plurality of patient response data;
   initiating a second phase of treatment, wherein the second phase of treatment comprises implanting a macrostimulator module at a second anatomical location that is different than the first anatomical location, wherein said second anatomical location is a subcutaneous space within the patient, removing at least one of the power source or the power source and pulse generator, and coupling the macrostimulator module to the detachable lead positioned at the stimulation site; wherein the macrostimulator comprises a power source that has more energy than the power source of the microstimulator.

2. The method of claim 1, wherein said plurality of patient response data comprises at least one of patient symptoms, patient questionnaire responses, patient medication usage, pH levels in the patient's esophagus, impedance-based pH-metry, a manometry value of LES-EEP, esophagitis score, acid exposure events, physiological response, or a presence of Barrett's esophagus.

3. The method of claim 1, wherein the macrostimulator module comprises a pulse generator.

4. The method of claim 3, wherein the pulse generator of the macrostimulator module generates pulses having an amperage ranging from 0.1 mA to 10 mA, a frequency ranging from 1 Hz to 100 Hz, a duration ranging from 50 μsec to 1000 μsec, a duty cycle ranging from 1% to 100% and a pulse shape that is monopolar or bipolar.

5. The method of claim 1, wherein the detachable lead of the microstimulator module has a length in a range of 1 cm to 40 cm and a diameter in a range of 0.1 mm to 3 mm.

6. The method of claim 1, wherein a detachable lead of the macrostimulator module has a length ranging from 1 cm to 100 cm and a diameter ranging from 0.5 mm to 4 mm.

7. The method of claim 1, wherein the power source module is rechargeable.

8. The method of claim 1, wherein the power source module is non-rechargeable.

9. The method of claim 1, wherein the power source module has a capacity ranging from 1 mAh to 1000 mAh.

10. The method of claim 1, wherein the power source of the macrostimulator module is rechargeable.

11. The method of claim 1, wherein the power source of the macrostimulator module is non-rechargeable.

12. The method of claim 1, wherein the power source of the macrostimulator module has a capacity ranging from 100 mAh to 5000 mAh.

13. The method of claim 1, wherein said plurality of pulses are defined by an amperage ranging from 0.1 mA to 10 mA, a frequency ranging from 1 Hz to 100 Hz, a duration ranging from 50 μsec to 1000 μsec, a duty cycle ranging from 1% to 100% and a pulse shape that is monopolar or bipolar.

14. The method of claim 13, wherein, during the first phase of treatment, at least one of a treatment site, the amperage of the plurality of pulses, the frequency of the plurality of pulses, the duration of the plurality of pulses, the duty cycle of the plurality of pulses, or the pulse shape of the plurality of pulses is modified at least once.

15. The method of claim 1, wherein said first phase of treatment is performed for a period of less than 90 days.

16. The method of claim 1, wherein said second phase of treatment is performed for a period greater than 90 days.

17. The method of claim 1, wherein the power source module is detachably attached to said pulse generator of the microstimulator module through an intermediate lead.

* * * * *